US010234463B2

(12) United States Patent
Mayr et al.

(10) Patent No.: US 10,234,463 B2
(45) Date of Patent: Mar. 19, 2019

(54) AIDING ASSESSMENT OF PROGNOSIS IN INFLAMMATORY DISEASE BY MEASURING OCTAMERIC PTX$_3$

(71) Applicant: KING'S COLLEGE LONDON, London (GB)

(72) Inventors: Manuel Mayr, London (GB); Friederike Cuello, London (GB)

(73) Assignee: KING'S COLLEGE LONDON, London (GB)

( * ) Notice: Subject to any disclaimer, the term of this patent is extended or adjusted under 35 U.S.C. 154(b) by 0 days.

(21) Appl. No.: 14/893,341

(22) PCT Filed: May 20, 2014

(86) PCT No.: PCT/GB2014/051583
§ 371 (c)(1),
(2) Date: Nov. 23, 2015

(87) PCT Pub. No.: WO2014/188206
PCT Pub. Date: Nov. 27, 2014

(65) Prior Publication Data
US 2016/0123994 A1 May 5, 2016

(30) Foreign Application Priority Data
May 24, 2013 (GB) .................................. 1309358.8

(51) Int. Cl.
*G01N 33/48* (2006.01)
*G01N 33/68* (2006.01)
(52) U.S. Cl.
CPC ..... *G01N 33/6893* (2013.01); *G01N 2333/47* (2013.01); *G01N 2333/4715* (2013.01);
(Continued)

(58) Field of Classification Search
None
See application file for complete search history.

(56) References Cited

FOREIGN PATENT DOCUMENTS

WO 2008078344 A1 7/2008

OTHER PUBLICATIONS

Inforzato, A., et al. J. Biol. Chem. (2008). 283(15); pp. 10147-10161.*

(Continued)

*Primary Examiner* — Kevin S Orwig
(74) *Attorney, Agent, or Firm* — Kenealy Vaidya LLP

(57) ABSTRACT

Some embodiments are directed to a method of collecting information useful in predicting clinical outcome in a subject, the method including providing a sample from said subject, and determining the level of octameric PTX3 in said sample, wherein determining the level of octameric PTX3 includes measuring the total amount of PTX3 present, and measuring the amount of octameric PTX3 present, and calculating the proportion of total PTX3 which is present as octamer, wherein if the proportion of octameric PTX3 is greater than 50%, the subject is identified as a likely non-survivor. Some embodiments are also directed to a method of collecting information useful in predicting clinical outcome in a subject, the method including providing a sample from said subject, and determining the level of octameric PTX3 in said sample, wherein an elevated level of octameric PTX3 compared to a reference level indicates a reduced likelihood of survival.

13 Claims, 13 Drawing Sheets
Specification includes a Sequence Listing.

(52) U.S. Cl.
CPC ..... *G01N 2800/26* (2013.01); *G01N 2800/52* (2013.01); *G01N 2800/7095* (2013.01)

(56) References Cited

OTHER PUBLICATIONS

Inoue, K., et al. Int. J. Vasc. Med. (2012). 2012; pp. 1-6; article ID 657025.*
Inoue, K., et al. Arterioscler. Thromb. Vasc. Biol. (2007). 27(1); pp. 161-167.*
Mauri, T., et al. Intensive Care Med. (2010). 36; pp. 621-629.*
International Search Report issued in International Application No. PCT/GB2014/051583.
Written Opinion of the International Searching Authority issued in International Application No. PCT/GB2014/051583.
Renate Schnabel, et al., "Selenium supplementation improves antioxidant capacity in vitro and in vivo in patients with coronary artery disease: The SElenium Therapy in Coronary Artery disease Patients (SETCAP) Study," American Heart Journal, Dec. 2008, vol. 156, Issue 6, pp. 1201.e1-1201.e11.
Matthias Angstwurm, et al., "Selenium replacement in patients with severe systemic inflammatory response syndrome improves clinical outcome," Critical Care Medicine, Oct. 1999; vol. 27, Issue 9, pp. 1807-1813.
Beat Muller, et al., "Circulating levels of the long pentraxin PTX3 correlate with severity of infection in critically ill patients," Critical Care Medicine, Jul. 2001; vol. 29, Issue 7, pp. 1404-1407.
Raija Uusitalo-Seppälä, et al., "Pentraxin 3 (PTX3) Is Associated with Severe Sepsis and Fatal Disease in Emergency Room Patients with Suspected Infection: A Prospective Cohort Study," PLoS ONE, Jan. 2013; vol. 8, Issue 1, p. e53661.
Antonio Inforzato, et al., "The Angiogenic Inhibitor Long Pentraxin PTX3 Forms an Asymmetric Octamer with Two Binding Sites for FGF2" The Journal of Biological Chemistry, Jun. 2010; vol. 285, Issue 23, pp. 17681-17692.
Jyoti Balhara, et al., "Pentraxin 3: An Immuno-Regulator in the Lungs,", Frontiers in Immunology, Jan. 2013, vol. 4, Issue 1, pp. 1-10.

* cited by examiner

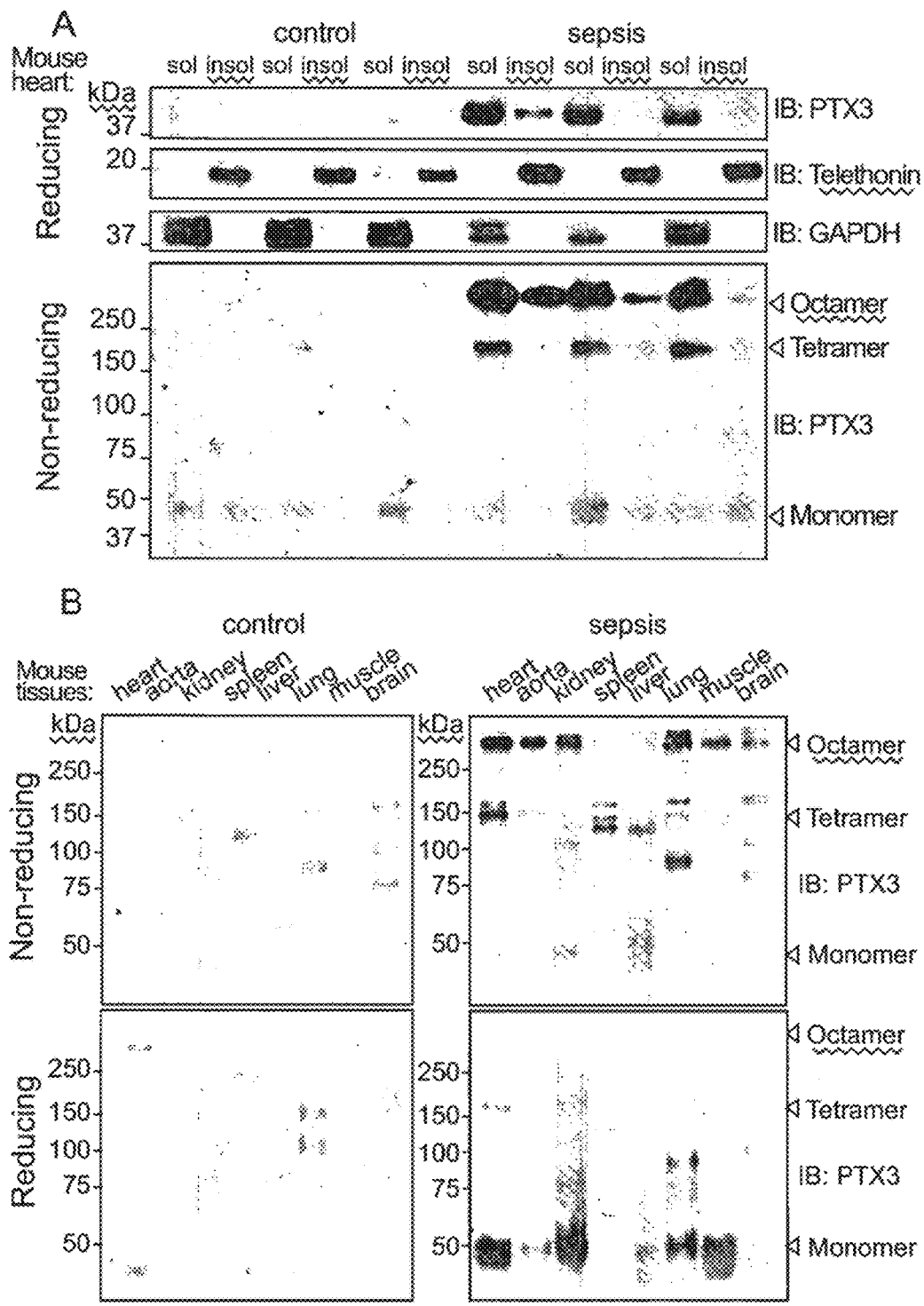

C

A

C

A

B

SEQUENCE LISTING

```
<160> NUMBER OF SEQ ID NOS: 1

<210> SEQ ID NO 1
<211> LENGTH: 381
<212> TYPE: PRT
<213> ORGANISM: Homo sapiens

<400> SEQUENCE: 1

Met His Leu Leu Ala Ile Leu Phe Cys Ala Leu Trp Ser Ala Val Leu
1               5                   10                  15

Ala Glu Asn Ser Asp Asp Tyr Asp Leu Met Tyr Val Asn Leu Asp Asn
            20                  25                  30

Glu Ile Asp Asn Gly Leu His Pro Thr Glu Asp Pro Thr Pro Cys Ala
        35                  40                  45

Cys Gly Gln Glu His Ser Glu Trp Asp Lys Leu Phe Ile Met Leu Glu
    50                  55                  60

Asn Ser Gln Met Arg Glu Arg Met Leu Leu Gln Ala Thr Asp Asp Val
65                  70                  75                  80

Leu Arg Gly Glu Leu Gln Arg Leu Arg Glu Glu Leu Gly Arg Leu Ala
                85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
        115                 120                 125

Arg Arg Leu Ala Arg Met Glu Gly Ala Glu Ala Gln Arg Pro Glu Glu
    130                 135                 140

Ala Gly Arg Ala Leu Ala Ala Val Leu Glu Glu Leu Arg Gln Thr Arg
145                 150                 155                 160

Ala Asp Leu His Ala Val Gln Gly Trp Ala Ala Arg Ser Trp Leu Pro
                165                 170                 175
```

```
Ala Gly Cys Glu Thr Ala Ile Leu Phe Pro Met Arg Ser Lys Lys Ile
            180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
        210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Gly Glu Glu Asn Lys Leu
            245                 250                 255

Val Ala Glu Ala Met Val Ser Leu Gly Arg Trp Thr His Leu Cys Gly
            260                 265                 270

Thr Trp Asn Ser Glu Glu Gly Leu Thr Ser Leu Trp Val Asn Gly Glu
        275                 280                 285

Leu Ala Ala Thr Thr Val Glu Met Ala Thr Gly His Ile Val Pro Glu
        290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
            325                 330                 335

Asn Ile Trp Asp Ser Val Leu Ser Asn Glu Glu Ile Arg Glu Thr Gly
            340                 345                 350

Gly Ala Glu Ser Cys His Ile Arg Gly Asn Ile Val Gly Trp Gly Val
        355                 360                 365

Thr Glu Ile Gln Pro His Gly Gly Ala Gln Tyr Val Ser
        370                 375                 380
```

AIDING ASSESSMENT OF PROGNOSIS IN INFLAMMATORY DISEASE BY MEASURING OCTAMERIC PTX$_3$

CROSS REFERENCE TO RELATED APPLICATION

This application is a National Phase filing under 35 C.F.R. § 371 of and claims priority to PCT Patent Application No.: PCT/GB2014/051583, filed on May 22, 2014, which claims the priority benefit under 35 U.S.C. § 119 of British Application No.: 1309358.8, filed on May 24, 2013, the contents of which are hereby incorporated in their entireties by reference.

FIELD OF THE INVENTION

The invention relates to assessment of subjects suffering from inflammatory disease, for example oxidative stress in an inflammatory disease. In particular the invention relates to aiding the assessment of the prognosis of such subjects, and/or their response to treatment.

BACKGROUND TO THE INVENTION

Many patients with a severe acute illness have overwhelming systemic inflammation causing extensive tissue injury and multiple organ dysfunction syndrome (MODS). MODS is common, associated with high mortality, short-term morbidity, and significant chronic illness. When it develops, artificial organ support in an intensive care unit (ICU) is usually required. Despite prompt treatment with antibiotics and supportive care, effective therapy is not available yet. Disease manifestation involves a major inflammatory response accompanied by hypotension, vascular hyporeactivity, and cardiac depression. The latter is reversible and probably mediated by the synergistic effects of inflammatory cytokines and nitric oxide. In contrast, other organs, such as lungs, kidneys, and liver may quickly fail. MODS occurring in ICU patients is frequently deadly. Therefore, early categorisation of patients with different prognoses is important, but proves difficult in the prior art. Another problem in the art is the absence of a timely and/or specific biomarker for disease outcome.

Severe sepsis [SS] is a common acute illness in intensive care units [ICU] with high mortality rates and chronic morbidity. When associated with cardiovascular failure [termed septic shock] mortality rate is very high [50-80%]. A problem in the art is the lack of availability of biomarkers (such as organ specific biomarkers) that enable early diagnosis of impending septic shock to accurately categorise patients for personalised and focused interventions. There are approximately 30,000 annual cases of SS in the UK and numbers are rising. An uncontrolled inflammatory response to infection causes damage to and subsequently failure of organs such as the lungs, heart and kidneys. The underlying mechanisms are unclear. Medical care of patients combines prompt treatment with antibiotics and supportive care and often requires artificial organ support provided in an ICU. However, despite over 200 sepsis randomised controlled trials since 1992, no effective therapies exist. Consequently, an estimated 200,000 US ICU patients die every year. Hence, there is a need in the art for specific biomarkers that allow clinicians to, in real time, risk-stratify, initiate appropriate therapies, and/or accurately track response to treatment.

No existing biomarker reliably predicts mortality or response to treatment. Bedside clinicians are therefore unable to reliably predict risk of death, or monitor biological response to treatment. While >100 different potential sepsis biomarkers have been assessed, none has sufficient specificity or sensitivity to be clinically helpful. Common examples include C-reactive protein (CRP) and procalcitonin (PCT). Neither reliably predicts mortality. Neither is associated with treatment response.

Inforzato et al (2010 The Journal of Biological Chemistry, Volume 285, page 17681 to 17692) report that Pentraxin (PTX3) forms an asymmetric octamer. Biophysical studies of PTX3 are disclosed. Both recombinant and native human PTX3 molecules are studied. It is taught that the protein is composed of eight identical protomer sub-units. The structure of the assembled octamer is described. The assembled octamer is considered to be an asymmetric structure, consisting of two differently sized lobe regions connected by a stalk region. The authors consider that the N-terminal domain of the protomer provides the main structural determinant underlying this quaternary organisation. It is taught that the PTX3 octamer contains two FGF2 binding sites, whereas it is the tetramers that act as the functional units in ligand recognition. Inforzato et al do not disclose any connection between the different oligomeric PTX3s and any medical condition. Inforzato et al is confined to structural/biophysical characterisation of PTX3.

Inforzato et al (2008 The Journal of Biological Chemistry, Volume 283, pages 10147 to 10161) report study of the structural characterisation of PTX3, and its role in cumulus matrix organisation. The authors used both native and denaturing PAGE analysis and concluded that PTX3 is mainly composed of covalently linked octamers. The authors also studied PTX3 using mass spectrometry as well as cysteine/serine site directed mutagenesis. As a result of their studies, the authors report that cysteine residues at positions 47, 49 and 103 in the N-terminal domain of PTX3 are important for stabilising the tetrameric form of PTX3. They further report that cysteines at positions 317 and 318 are involved in linking PTX3 tetramers to form PTX3 octamers. The authors go on to produce a refined model of PTX3 structure, taking into account intrachain disulphide bonds. The authors study mutated PTX3 in a system rescuing defective cumulus matrix organisation, which is connected to ovulation. The authors found that PTX3 tetramers exhibited wild type rescue activity, whereas mutant PTX3 in the form of dimers had impaired functionality. The authors concluded that PTX3 tetramers were the functional molecular units required for cumulus matrix organisation and stabilisation. There is no teaching in this document regarding the importance of PTX3 octamers.

Rady (2007 Journal of Intensive Care Medicine, Volume 22, pages 386 to 388) presents an editorial article reviewing the field of sepsis and multi-organ dysfunction. In particular, the author discusses the cause-effect relationship of biomarkers in sepsis. In more detail, the author presents a detailed analysis of the field and study of B-type natriuretic peptide (BNP), and its use in sepsis and as a predictor of clinical outcome. BNP is a dominant marker in the field of sepsis. This document does not deal with PTX3. The author concludes that the cause-effect relationship of biomarkers is sepsis and clinical outcome remains elusive.

Further research regarding BNP and its correlation to disease outcome is presented by Rivers et al (2007 Journal of Intensive Care Medicine Volume 22, pages 363 to 373). The authors present a detailed study of the value of BNP, including its diagnostic, therapeutic and prognostic utility in critically ill patients. The authors present time course studies tracking BNP levels in patients with severe sepsis and septic shock. The authors draw robust conclusions about the value of BNP as a marker in this setting. Statistically significant associations are reported for BNP levels and organ dysfunction, myocardial dysfunction, global tissue hypoxia and mortality. Thus, the authors teach BNP as a useful and reliable marker in the early detection, stratification, treatment and prognostication of patients at high risk. This study does not discuss PTX3.

Pierrakos and Vincent (2010 Critical Care Volume 14, pages 1 to 18) present a literature review of biomarkers in sepsis. The authors searched scientific literature databases using various keywords. Their searching covered 3370 references involving 178 different biomarkers. The authors discuss the fact that many biomarkers have been evaluated for use in sepsis. They also remark that most of the biomarkers had been tested clinically, but relatively few had been used for diagnosis. PTX3 (Pentraxin 3) is mentioned in table to, line 26 of this document as being distinguished between septic shock and SIRS. None of the biomarkers reviewed had sufficient specificity or sensitivity to be employed in clinical practice. There is no disclosure in Pierrakos and Vincent of any of the multimeric states of PTX3.

US 2010/0292131 discloses kits and methods for the diagnosis, prognosis and prediction of sepsis in a subject, or for the differentiation between sepsis and SIRS in a subject. The disclosure is focussed on measuring the levels of pro-hepcidin (pro-HEPC) and/or a measurement of certain histone proteins. Pentraxin 3 is mentioned in this document as one of a panel of further biomarkers, which can be assayed simultaneously with the main markers being studied. This document does not appear to disclose information regarding the multimeric states of PTX3.

EP 2 092 342 B1 discloses a method for measuring plasma levels of pentraxin (PTX3). In particular, this document discloses a method for measuring PTX3 levels in plasma samples, comprising treating the sample with an agglutinating agent before determining the levels of PTX3. There is no disclosure or discussion in this document of PTX3 multimers.

Muller et al (2001 Critical Care Medicine Volume 29, pages 1404 to 1407) discloses how circulating levels of the long pentraxin PTX3 correlate with severity of infection in critically ill patients. The authors compare PTX3 with the more established marker C-reactive protein (CRP) in critically ill patients. The authors conclude that PTX3 is elevated in critically ill patients and correlates with severity of disease and infection. The authors do not deal with the multimeric forms of PTX3 in this disclosure.

Mauri et al (2010 Intensive Care Medicine Volume 36, pages 621 to 629) disclose persisting high levels of plasma PTX3 over the first days after severe sepsis and septic shock onset are associated with mortality. Ninety patients were studied. Patients were enrolled into the study on admission into intensive care. PTX3 levels were measured at various intervals.

Mortality was recorded at ninety days. The authors concluded that persisting high levels of circulating PTX3 over the first days from sepsis onset may be associated with mortality. They also concluded that PTX3 correlates with severity of sepsis and with sepsis associated coagulation/fibrinolysis dysfunction. The authors did not consider or assess PTX3 multimerisation.

Vänskä et al (2011 Haematologica Volume 96, pages 1385 to 1389) disclose that high Pentraxin 3 level predicts septic shock and bacteremia at the onset of febrile neutropenia after intensive chemotherapy of haematologic patients. The authors measured PTX3 and CRP in their study. The authors concluded that PTX3 is an early predictor of complications in haematologic patients with neutropenic fever. They also concluded that high PTX3 predicts septic shock and bacteremia already at the onset of febrile neutropenia. The authors did not examine the multimeric state of PTX3, but only assessed total PTX3 levels.

Daigo et al (2012 Molecular and Cellular Proteomics Volume 11, pages 1 to 12) disclose that the proteomic profile of circulating pentraxin 3 complex in sepsis demonstrates the interaction with azurocidin 1 and other components of the neutrophil extracellular trap. The authors used shotgun proteomics of circulating PTX3 complexes in order to study PTX3 ligands. The authors identified 104 candidate proteins, including various known PTX3 interacting proteins. The authors went on to show direct interaction of bactericidal proteins such as azurocidin 1 and myeloperoxidase with PTX3. Discussion of PTX3 oligomerisation appears to be confined to testing whether or not AZU1 binding required the known PTX3 N-terminal domain oligomer, as is the case for FGF2-PTX3 interaction. The authors conclude that AZU1-PTX3 binding is by a mechanism similar to PTX3-FGF2 binding. There is no study of PTX3 oligomers themselves in this publication.

Uusitalo-Seppälä et al (2013 Plos One Volume 8, pages E53661) disclose that pentraxin 3 is associated with severe sepsis and fatal disease in emergency room patients with suspected infection. The authors measured plasma PTX3 levels using commercially available solid-phase ELISA test on admission to emergency rooms. The authors compared PTX3 levels to CRP levels and PCT levels. The authors found that a high PTX3 concentration predicted severe disease and poor outcome. There is no discussion of, nor study of, PTX3 oligomerisation in this report.

The present invention seeks to overcome the problems associated with the prior art.

SUMMARY OF THE INVENTION

It is known in the art to assess PTX3 levels. It is known in the art that PTX3 is associated with severe sepsis. It is known in the art that PTX3 is associated with fatal disease, for example in ICU patient admissions. However, in the art it is only ever total PTX3 levels which have been assessed. PTX3 is treated in the art as a single substance. Measuring PTX3 in the art consists of determining the total PTX3 levels present in a subject or sample.

In contrast, the present inventors have studied multimeric forms of PTX3. PTX3 can exist as a monomer, a tetramer or an octamer. The present inventors have made surprising discoveries, in particular in connection with the octamer. More specifically, the inventors have identified a robust and statistically significant relationship between the PTX3 octamer and the degree of oxidative stress in the subject. More importantly, the inventors have demonstrated that assessing octameric PTX3 levels contributes valuable information to the prognosis of the subject. The invention is based upon these remarkable findings.

Thus, in one aspect the invention provides a method of collecting information useful in predicting clinical outcome in a subject, the method comprising providing a sample from said subject, and determining the level of octameric PTX3 in said sample, wherein determining the level of octameric PTX3 comprises measuring the total amount of PTX3 present, and measuring the amount of octameric PTX3 present, and calculating the proportion of total PTX3 which is present as octamer, wherein if the proportion of octameric PTX3 is greater than 50%, the subject is identified as a likely non-survivor.

A high proportion (e.g. >50%) of octameric PTX3 is associated with a greater likelihood of an adverse outcome.

In another aspect, the invention relates to a method of collecting information useful in predicting clinical outcome in a subject, the method comprising providing a sample from said subject, and determining the level of octameric PTX3 in said sample, wherein an elevated level of octameric PTX3 compared to a reference level indicates a reduced likelihood of survival.

The reference level may be a value previously determined for a healthy subject, or may be a value determined for the same subject, for example a level determined at an earlier time point for the same subject. This is discussed in more detail below.

In another aspect, the invention relates to a method as described above wherein the ratio of octameric PTX3 to monomeric PTX3 is determined. The additional advantages of using the ratio of octameric PTX3 to monomeric PTX3 are described below, for example with reference to the drawings where the ROC curves can be found.

Suitably determining the level of octameric PTX3 comprises determining the ratio of octameric PTX3 to monomeric PTX3. In embodiments where the ratio is determined, references to the level of PTX3 must be interpreted accordingly, and may require determination of the level of monomeric PTX3 as well as octameric PTX3 (rather than determination of the level of total PTX3 as well as octameric PTX3).

Thus in one aspect the invention provides a method of collecting information useful in predicting clinical outcome in a subject, the method comprising providing a sample from said subject, and determining the ratio of octameric PTX3 to monomeric PTX3 in said sample, wherein determining the ratio of octameric PTX3 to monomeric PTX3 comprises measuring the amount of octameric PTX3 present, and measuring the amount of monomeric PTX3 present, and calculating the ratio of octameric PTX3 to monomeric PTX3, wherein if the ratio of octameric PTX3 to monomeric PTX3 is elevated, the subject is identified as a likely non-survivor.

In another aspect, the invention relates to a method as described above wherein the amounts of monomeric PTX3 and octameric PTX3 are determined by the steps of
a) separating the proteins in the sample under non-reducing conditions;
b) determining the amounts of monomeric PTX3 and octameric PTX3 by quantifying the amounts of those forms of PTX3 as separated in step (a).

Suitably step (b) comprises blotting the separated proteins on to a membrane and quantifying the amounts of those forms of PTX3 on said membrane.

Suitably the amounts of monomeric PTX3 and octameric PTX3 are determined by mass spectrometry.

Suitably the subject has or is suspected of having an inflammatory disease.

Suitably said inflammatory disease is sepsis, cardiovascular disease or a rheumatoid disease.

Suitably said inflammatory disease is sepsis.

Suitably said sepsis is severe sepsis or septic shock. Suitably said sepsis is severe sepsis.

Suitably said subject is experiencing oxidative stress in said inflammatory disease.

Suitably the sample comprises blood or plasma, most suitably plasma.

Suitably the measurement is repeated at a predetermined time interval.

Suitably said time interval is daily.

In another aspect, the invention relates to a method of identifying a patient at risk of acute organ failure, comprising performing the method as described above wherein detection of elevated octameric PTX3, or elevated ratio of octameric PTX3 to monomeric PTX3, indicates an increased likelihood of acute organ failure.

In another aspect, the invention relates to a method of monitoring a subject's response to treatment comprising performing the method as described above at at least two different time points and comparing the levels of octameric PTX3 at those at least two different time points, wherein observing a decreasing level of octameric PTX3, or decreasing ratio of octameric PTX3 to monomeric PTX3, in the later time point(s) indicates a positive response to treatment.

In another aspect, the invention relates to a method of identifying a patient at risk of acute organ failure, comprising performing the method as described above wherein detection of elevated ratio of octameric to monomeric PTX3 indicates an increased likelihood of acute organ failure.

In another aspect, the invention relates to a method of monitoring a subject's response to treatment comprising performing the method as described above at at least two different time points and comparing the levels of octameric PTX3, or the ratios of octameric to monomeric PTX3, at those at least two different time points, wherein observing a decreasing level of octameric PTX3, or a decreasing ratio of octameric to monomeric PTX3, in the later time point(s) indicates a positive response to treatment.

In another aspect, the invention relates to a method of treating a patient suffering from inflammatory disease comprising performing the method as described above wherein if an increased level of octameric PTX3, or increased ratio of octameric PTX3 to monomeric PTX3, is observed, a treatment or medicament is administered to said subject, said treatment or medicament suitably selected from an antioxidant (e.g. selenium, N-Acetyl cysteine), a drug to improve cardiac function (e.g. Levosimenden, PDE inhibitors such as Milrinone (Yano et al 2000, Am. J. Physiol. vol. 279, H1898-H1905)), and a statin, preferably a statin.

In another aspect, the invention relates to a method of collecting information useful in aiding the prognosis of a subject suffering from oxidative stress comprising performing the method as described above, wherein an elevated level of octameric PTX3, or elevated ratio of octameric PTX3 to monomeric PTX3, indicates a negative prognosis.

In another aspect, the invention relates to a method of collecting information useful in predicting clinical outcome in a subject, the method comprising providing a sample from said subject and determining the level of monomeric PTX3 in said sample, wherein determining the level of monomeric PTX3 comprises measuring the total amount of PTX3 present, and measuring the amount of monomeric PTX3 present, and calculating the proportion of total PTX3 which is present as monomer, wherein if the proportion of monomeric PTX3 is greater than 90%, the subject is identified as a probable survivor.

Suitably if the proportion of monomeric PTX3 is less than 20%, the subject is identified as a probable non-survivor.

Suitably if the proportion of monomeric PTX3 is less than 20%, the subject is identified as a non-responder to momentous treatment. It may be appropriate to administer a change or intensification of therapeutic intervention to a subject so identified.

In one embodiment determining the level of octameric PTX3 in said sample comprises contacting said sample with a reagent capable of binding to said PTX3 and inferring the amount of PTX3 from the amount of reagent bound. This step may be preceded by a separation step allowing determination of the monomeric or multimeric state of the PTX3 so detected. An example of a reagent capable of binding to said PTX3 is an anti-PTX3 antibody.

In one embodiment determining the level of octameric PTX3 in said sample comprises introducing said sample to an apparatus capable of determining the masses of the molecules in said sample and inferring the amount of PTX3 from the data output by said apparatus. An example of such apparatus is a mass spectrometer.

DETAILED DESCRIPTION OF THE INVENTION

Over the past decade, the field of proteomics has made impressive progress. The plasma proteome, however, is the most complex proteome of the human body[2], and to date it is still challenging to detect the minor components directly in body fluids[3]. As an alternative strategy, the inventors applied proteomics to diseased cardiac tissue[4], where potential biomarkers are less dilute-7. For the proteomic investigations described herein, the inventors chose a septic mouse model to identify biomarker candidates. Validation was then performed using plasma samples from sepsis patients admitted ICUs. It is taught herein for the first time that assessing the oxidation state of inflammatory biomarkers, such as pentraxin-3 (PTX3), provides a superior predictor of disease outcome in patients suffering from an inflammatory disease, particularly an inflammatory disease comprising oxidative stress, such as septic patients.

By PTX3 we mean mammalian pentraxin 3, suitably human pentraxin 3 polypeptide. The reference sequence for this is Uniprot accession number P26022.

Sequences deposited in databases can change over time. Suitably the current version is used.

Suitably the database is UniProt release 2013_05 (1 May 2013).

Suitably the sequence is as shown below:

```
sp|P26022|PTX3_HUMAN Pentraxin-related protein
PTX3 OS = Homo sapiens GN = PTX3 PE = 1 SV = 3
MHLLAILFCALWSAVLAENSDDYDLMYVNLDNEIDNGLHPTEDPTPCACG

QEHSEWDKLFIMLENSQMRERMLLQATDDVLRGELQRLREELGRLAESLA

RPCAPGAPAEARLTSALDELLQATRDAGRRLARMEGAEAQRPEEAGRALA

AVLEELRQTRADLHAVQGWAARSWLPAGCETAILFPMRSKKIFGSVHPVR

PMRLESFSACIWVKATDVLNKTILFSYGTKRNPYEIQLYLSYQSIVFVVG

GEENKLVAEAMVSLGRWTHLCGTWNSEEGLTSLWVNGELAATTVEMATGH

IVPEGGILQIGQEKNGCCVGGGFDETLAFSGRLTGFNIWDSVLSNEEIRE

TGGAESCHIRGNIVGWGVTEIQPHGGAQYVS
```

The inventors undertook an unbiased proteomic screen. They conducted this screen in a mouse sepsis model. When analysing the samples, they noticed that pentraxin-3 (PTX3) was surprisingly found in the insoluble fraction of their samples. This was very surprising. The protein should not have been detected in the insoluble fraction, due to the sample preparation techniques which were used. The expectation was that the protein would have collected in serum plasma. Upon studying this surprising anomaly, the inventors discovered that it was an octameric form of pentraxin-3. Without wishing to be bound by theory, it appears that the octameric form of PTX3 may be trapped in the extracellular space and/or may imprint inflammation onto the tissue in which it is found.

In the course of their studies, the inventors also identified myeloperoxidase as the potential oxidase responsible for certain underlying events (see Table 1). In particular, this is found in neutrophils where it generates free radicals to kill bacteria. PTX3 may be involved in the neutrophil extracellular trap, which is also implicated in various damaging patient states such as atherosclerosis/cardiovascular disease. Thus, in one embodiment, the invention relates to use of PTX-3 as a marker of neutrophil extracellular trap formation.

We describe a novel marker that can identify patients with septic shock who are at risk of death, and determine their response to treatment. Using proteomics, we have made a novel observation: pentraxin-3, a protein that is known to rise in septic shock, is oxidized in blood and the different oxidation states provide a superior predictor of disease outcome over the conventional measurements of this protein and other markers of cardiac tissue damage.

In one embodiment the invention relates to oxidised pentraxin 3 as a novel biomarker for survival in sepsis.

Using a systematic proteomics approach in a preclinical model of sepsis we identified pentraxin-3 as lead candidate, but also made the novel observations that this protein was present in an oxidised form, and that its oxidation state was associated with poor disease outcome in patients. Pentraxin-3 is barely detectable in plasma of healthy individuals, but increases up to 100-fold in sepsis depending on the severity of the disease. Conventional prior art measurements of inflammatory biomarkers have a distinct weakness that the protein levels tend to remain high even after admission to ICU. In contrast, advantageously the marker of the invention (oxidation state of PTX3) normalises rapidly in responders to therapy. For example, on day 2 post-admission to ICU, oxidised PTX3 was undetectable in survivors, but still constituted more than half of the total protein in non-survivors (see examples section and accompanying drawings).

We have applied a systematic proteomics approach for biomarker discovery in a preclinical model of sepsis. Among the most differentially expressed proteins was an acute phase protein that is known to be associated with increased mortality in septic patients. Interestingly, pentraxin-3 accumulated as a multimer due to disulphide-bond formation, most notably in hearts, aortas, kidneys and lungs—organs that are susceptible to septic complications. The oxidized isoform was also detected in plasma and serum. When we quantified the different oxidation states in septic patients over a time course of 11 days, there was no difference between survivors and non-survivors on admission to ICU. Already by day 2, however, a reduction of the oxidized multimeric to the reduced monomeric isoform was associated with better chances of survival to 28 days of follow-up. This despite total protein levels remaining unchanged. This is in stark contrast to prior art techniques which only assay PTX3 protein levels, and do not consider the oxidation state of PTX3.

Medical Applications

The invention provides a method of assessing oxidative stress, suitably response to oxidative stress. Suitably this is oxidative stress in inflammation.

The invention relates to the assessment of inflammatory disease. Inflammatory disease embraces a range of conditions. One example of an inflammatory disease to which the invention may be applied is sepsis. Sepsis is an acute inflammatory disease, in particular an acute inflammatory cardiovascular disease, such as a disease involving the cardiovascular system.

An inflammatory disease to which the invention may be applied is cardiovascular disease. Cardiovascular disease is a chronic inflammatory disease. Cardiovascular disease may be one or more of MI, AF, A. pectoris, atherosclerosis, transient ischaemic attacks, stroke, peripheral vascular disease, cardiomyopathy and/or heart failure.

An inflammatory disease to which the invention may be applied is a rheumatoid disease.

In one embodiment, the invention may be applied to assess neutrophil activation, such as neutrophil activation leading to neutrophil extracellular trap formation.

Most suitably, the invention is applied to the assessment of oxidative stress in inflammatory disease.

Most suitably, the invention is applied to prediction of patient outcomes in inflammatory disease such as oxidative stress in inflammatory disease.

In one aspect the invention relates to a method of aiding the assessment of prognosis of a subject comprising inferring from the amount of octameric PTX3 present in a sample from said subject the likelihood of survival of said subject.

In one aspect the invention relates to a method of aiding the assessment of prognosis of a subject comprising inferring from the amount of octameric PTX3 present in a sample from said subject the likely response of said subject to therapy or treatment.

Sepsis

Despite prompt treatment, sepsis is still associated with significant mortality. Thus there is a need in the art for novel independent prognostic biomarkers to predict disease outcome. Oxidated PTX3 is an example of such a marker according to the present invention.

Patients in an intensive care unit are typically receiving intensive therapy. In the prior art, it is difficult or impossible to understand the likely outcomes for individual patients during therapy. However, the invention advantageously enables us to assess the likely outcomes (prognosis) of patients in this setting. More specifically, by assessing the levels of octameric PTX3 in patients receiving intensive therapy, probable outcomes may be predicted.

Increased levels of octameric PTX3 indicate a lower likelihood of survival.

Increased levels of octameric PTX3 may indicate administration of intensified treatment and/or monitoring, or may indicate an extended stay in ICU.

Lower levels of octameric PTX3 indicate a higher likelihood of survival.

Lower levels of octameric PTX3 may indicate earlier release from ICU.

It is an advantage of the invention that therapies or treatments provided to subjects may be tailored according to the results of the test. For example, patients exhibiting higher levels of octameric PTX3 are less likely to survive. Therefore, a more radical medical intervention may be indicated for a patient showing a higher level of octameric PTX3. For example, subjects showing a high octameric PTX3 may be administered a higher risk treatment, or may be administered a more intensive treatment. For example, patients showing high octameric PTX3 may be administered haemo-dialysis. For example, patients showing high octameric PTX3 may be provided with treatment earlier than patients showing a lower octameric PTX3.

The invention provides advantages to healthcare providers as well as patients. For example, if a patient can be moved from an intensive care unit to an ordinary ward, there is a substantial cost saving to the institution providing their treatment. According to the invention, when a patient is observed to have a lower octameric PTX3 level, they are more likely to survive and are less likely to need intensive treatment. Therefore, it is possible to move patients showing lower octameric PTX3 to a lower category ward, such as moving them from an intensive care unit to a conventional hospital ward.

The invention provides advantages in the management of patients and family expectations. For example, patients showing a high octameric PTX3 level are less likely to survive. Appropriate counseling may be provided both to them and to their relatives, so that they are better prepared for possible negative outcomes.

It is an advantage of the invention that it allows attention and/or resources to be focussed on higher risk patients.

It is an advantage of the invention that it enables experimental treatments to be targeted to patients having the lowest probability of survival (the highest octameric PTX3 levels). These may include treatments which would not ordinarily be administered to patients having good prospects of survival.

In one embodiment, the invention relates to a method assessing response to therapy, wherein reduced octameric PTX3 following administration of the therapy is indicative of a positive response to said therapy, and/or wherein an increased level of octameric PTX3 following administration of the therapy shows an adverse reaction to said therapy.

In one aspect of the invention, the inventors teach that octameric PTX3 is a marker of oxidative stress.

In one embodiment the invention relates to a method of treating a patient comprising assessing their octameric PTX3 levels, wherein a subject showing elevated octameric PTX3 levels is administered an anti-inflammatory therapy such as cortisone or a statin, suitably a statin.

Application of Tests

The invention finds application in intensive care units or hospital wards. Subjects may advantageously be routinely tested on entry into ICU. Advantageously, patients may be monitored regularly, for example monitored daily, for their octameric PTX3 levels. Advantageously, a physician may review patients' octameric PTX3 collected at timed intervals. This has the advantage of allowing the physician to assess an improvement or worsening in the patients' conditions. This has the advantage of allowing the physician to provide individualised treatment to said patient.

The invention may be applied in the primary care/general practice setting. For example, patients presenting with possible cardiovascular disease or other chronic inflammatory disease such as rheumatoid disease may be tested for their octameric PTX3 levels according to the invention.

Timing

It will be apparent to the skilled reader that the timing of tests according to the invention may be important. For example, in acute conditions such as sepsis, and/or for patients being treated in an intensive care unit, a timecourse of octameric PTX3 can provide especially useful information. Timing is a less critical component of the methods of the invention for chronic conditions such as cardiovascular disease or rheumatoid disease when occasional (such as monthly, multi-monthly, half-yearly, annual or even longer) time intervals may be useful. The invention may also be useful in monitoring initial optimisation to treatment at the onset of disease or when worsening of the disease requires adjustment of the medication (WHO Stufenschema).

With acute conditions such as sepsis, the invention provides for regular testing, such as daily testing.

It should be noted that it is an advantage of the invention that it provides prognostic information for outcome in inflammatory conditions.

It should be noted that it is an advantage of the invention that it provides prognostic information for either acute or chronic conditions. The method according to the invention provides information useful when predicting future events or outcomes for the subject being tested.

Suitably when the condition or suspected condition is an acute condition, such as sepsis or such as monitoring ICU patients, the ratio of octameric PTX3 to monomeric PTX3 is determined. This has the advantage of greater discriminatory power as shown by the ROC curves in the drawings.

Suitably when the condition or suspected condition is a chronic condition, such as cardiovascular disease or rheumatoid disease, the detection of an elevated level of octameric PTX3, or even detection of the mere presence of octameric PTX3 (for example detection of PTX3 compared to a reference standard in which no octameric PTX3 is found corresponds to an elevated level of octameric PTX3), is useful in aiding determination of prognosis and/or predicting clinical outcome for a subject.

Without wishing to be bound by theory, analysis of the ratios of octameric PTX3 to monomeric PTX3 is also useful in chronic conditions. However, as a practical matter, the absolute amounts of PTX3 such as octameric PTX3 present in chronic conditions can be low and so for purely practical reasons it is often not desired to analyse ratios in chronic conditions since analysis of the level of (and/or proportion of) octameric PTX3 is advantageously carried out when addressing chronic conditions.

It is an advantage of the invention that assessment of oxidised (octameric) PTX3 is superior to the prior art testing of PTX3 which involves only assessing levels of total PTX3. For example the invention is superior in providing far better information.

The invention finds application in screening programmes. For example, the invention finds application in cardiovascular risk assessment. For example, the invention finds application in lipid programmes, such as hyperlipidemia screening. The invention finds application in testing of sugar related disorders, such as hyperglycaemia. The invention finds application in screening of blood pressure, such as elevated blood pressure screening.

Reference Standard

The reference standard typically refers to a sample from a healthy individual i.e. one who has not suffered inflammatory disease.

The reference standard can be an actual sample analysed in parallel. Alternatively the reference standard can be one or more values previously derived from a comparative sample e.g. a sample from a healthy subject. In such embodiments a mere numeric comparison may be made by comparing the value determined for the sample from the subject to the numeric value of a previously analysed reference sample. The advantage of this is not having to duplicate the analysis by determining concentrations in individual reference samples in parallel each time a sample from a subject is analysed.

Suitably the reference standard is matched to the subject being analysed e.g. by gender e.g. by age e.g. by ethnic background or other such criteria which are well known in the art. The reference standard may be a number such as an absolute concentration drawn up by one or more previous studies.

Reference standards may suitably be matched to specific patient sub-groups e.g. those with a previous relevant history such as a predisposition to inflammatory disease.

Reference standards may suitably be matched to an individual with a chronic disease to be useful during an inflammatory outburst (RA).

Suitably the reference standard is matched to the sample type being analysed. For example the concentration of the biomarker polypeptide(s) being assayed may vary depending on the type or nature of the sample. It will be immediately apparent to the skilled worker that the concentration value(s) for the reference standard should be for the same or a comparable sample to that being tested in the method(s) of the invention. For example, if the sample being assayed is blood then the reference standard value should be for blood to ensure that it is capable of meaningful cross-comparison and therefore a meaningful quantitative ratio being calculated. In particular, extreme care must be taken if inferences are attempted by comparison between concentrations determined for a subject of interest and concentrations determined for reference standards where the nature of the sample is non-identical between the two. Suitably the sample type for the reference standard and the sample type for the subject of interest are the same.

It should be noted that for some embodiments of the invention, the polypeptide/protein concentrations determined may be compared to a previous sample from the same subject. This can be beneficial in monitoring the progress of therapy in a subject. This can be beneficial in monitoring the course and/or effectiveness of a treatment of a subject. In this embodiment the method may comprise further step(s) of comparing the octameric PTX3 levels (or proportions or ratios) determined for the sample of interest to one or more octameric PTX3 levels (or proportions or ratios) determined for different samples such as samples taken at different time points for the same subject. Examples of time points include on admission to ICU, and/or day 2 after admission to ICU. By making such a comparison, information can be gathered about whether octameric PTX3 levels are increasing or decreasing in a particular subject. This information may be useful in monitoring or predicting changes over time, or changes inhibited or stimulated by a particular treatment or therapy regime, or any other variable of interest. Thus if octameric PTX3 levels are elevated, or elevated further, in a sample from a later time point from the same subject then this indicates a likelihood of prognosis such as prospects of survival worsening in said subject. Equally, if octameric PTX3 levels are decreased in a sample from a later time point from the same subject then this indicates a likelihood of improvement of prognosis such as prospects of survival in said subject. Clearly if these effects are observed in a subject undergoing treatment for inflammatory disease such as sepsis, then corresponding inferences regarding the effectiveness of the treatment may equally be drawn according to the present invention. In other words, when a subject is undergoing treatment, if octameric PTX3 levels are decreased in a sample from a later time point from the same subject then this indicates a likelihood that the treatment is effective; if octameric PTX3 levels are elevated, or elevated further, in a sample from a later time point from the same subject then this indicates a likelihood that the treatment is ineffective.

In this way, the invention can be used to determine whether, for example after treatment of the patient with a drug or candidate drug, the disease has progressed or not, or that the rate of disease progression has been modified. The result can lead to a prognosis of the outcome of the disease.

Cut Off Values

The table below shows calculations for a sliding cut-off for octamer levels. These are exemplary values at day 2. These exemplary values are as measured by densitometry from Western blots.

Reference is made to FIG. 7B—data in the table below corresponds to the AUC of FIG. 7B.

| Octamer PTX3 | ALIVE | | DEAD | | Test characteristics | | |
| --- | --- | --- | --- | --- | --- | --- | --- |
| | Freq. | Cum. Percent | Freq. | Cum. Percent | Definition of positive test result | Sensitivity | Specificity |
| | | | | | 100 | 0 | |
| 0 | 17 | 73.91 | 1 | 14.29 | >0 | 85.71 | 73.91 |
| 0.087 | 1 | 78.26 | | | >0.087 | 85.71 | 78.26 |
| 0.323 | | | 1 | 28.57 | >0.323 | 71.43 | 78.26 |
| 0.456 | 1 | 82.61 | | | >0.456 | 71.43 | 82.61 |
| 0.557 | | | 1 | 42.86 | >0.557 | 57.14 | 82.61 |
| 0.639 | 1 | 86.96 | | | >0.639 | 57.14 | 86.96 |
| 0.648 | | | 1 | 57.14 | >0.648 | 42.86 | 86.96 |
| 0.81 | 1 | 91.3 | | | >0.81 | 42.86 | 91.3 |
| 0.904 | 1 | 95.65 | | | >0.904 | 42.86 | 95.65 |
| 1.373 | | | 1 | 71.43 | >1.373 | 28.57 | 95.65 |
| 1.529 | 1 | 100 | | | >1.529 | 28.57 | 100 |
| 2.195 | | | 1 | 85.71 | >2.195 | 14.29 | 100 |
| 4.733 | | | 1 | 100 | >4.733 | 0 | 100 |

The choice of optimal cut-off depends on whether the operator wants to minimize false-positive and false negatives. In this example it is most important to identify as many of the non-survivors as possible. With a cut-off=0.1 for the octamer measured by densitometry, the sensitivity is 86% and the specificity is 78% (right hand two columns, row 3—marked with thick boxing in the table above).

The remainder of the table illustrates all other cut-offs which may be used for example in acute disease such as sepsis.

For chronic inflammation, the lowest cut-off should be used—the octamer is not detectable in healthy individuals. Any detectable octamer (value >0) should be considered a marker of oxidative stress and/or overwhelming inflammation.

Assay Format

It should be noted that oxidised and oxidated are synonyms. They have the same meaning. The terms oxidised and oxidated are used interchangeably in this document.

The invention is focussed on octameric PTX3. The octameric form is an oxidised form. Unless it is apparent from the context, mention of "oxidised PTX3" or "oxidated PTX3" may be taken to mean octameric PTX3.

The methods of the invention require assessment of the level of octameric PTX3. This is completely different to the prior art which teaches only assessment of total PTX3. By contrast, the invention makes clear that it is the level of the PTX3 octamer (the oxidised form of PTX3) which is important, such as prognostically important.

Assessment of octameric PTX3 may be accomplished by any means known in the art. Suitably, PTX3 may be separated into the different monomeric/multimeric forms. This may be accomplished by gel electrophoresis such as polyacrylamide gel electrophoresis (PAGE), for example non-reducing PAGE.

Suitably the sample is subjected to PAGE under non-reducing conditions. The resulting electrophoresed material may then be analysed to determine the level of the individual PTX3 species present. This may be done by mass spectrometry of the separated proteins. This may be done by blotting such as via a western blot onto an appropriate membrane. This membrane can then be probed with an anti-PTX3 antibody such as Epitomics Catalog#5414-1. This process may be referred to as immunoblotting. In this way, the different PTX3 species (monomers vs multimers) may be visualised. The total PTX3 present is determined by summing the individual amounts of the different PTX3 species detected. Alternatively, or in addition, the total PTX3 present may be determined by assessment of a parallel sample under reducing gel conditions.

In one embodiment, the sample comprising PTX3 may be divided into two or more parts, one part being subjected to PAGE under reducing conditions, and the other part being subjected to PAGE under non-reducing conditions. The resulting electrophoresed material may then be blotted such as via a western blot onto an appropriate membrane. This membrane can then be probed with an anti-PTX3 antibody. In this way, the different PTX3 species (monomers vs multimers) may be visualised in the non-reducing conditions. The total PTX3 should appear as a single species in the reducing conditions treatment, thereby facilitating easy quantification of the total PTX3 present.

It should be noted that there are at least three forms of PTX3. Firstly, there is the monomer (reduced form).

Secondly, there is the tetramer (four PTX3 molecules in a complex). Although levels of the tetramer are not believed to be important for the methods of the invention in the sense of association with a particular prognosis and/or likelihood of adverse outcome, levels of the tetramer may still provide a useful control value e.g. for normalisation of the relative octamer levels between individuals.

Lastly, there is the octameric (oxidised) form of PTX3 (eight PTX3 molecules in a complex).

Any mention of assessment of total PTX3 means assessment of the combined amount of PTX3 present, i.e. including the monomer, the tetramer and the octamer. The total level of PTX3 does not make any distinction between the monomeric/multimeric forms. The total PTX3 level may be determined directly, or may be determined by summing (adding) the individual levels of the monomer, the tetramer and the octamer.

Not only would the prior art of studying absolute levels of PTX3 not have led to the present invention, it would also have masked the present invention. The inventors teach for the first time that levels of oxidated (octameric) PTX3 is a key indicator of prognosis and/or response to treatment for patients suffering from inflammatory disease such as involving oxidative stress. It is a measure of this key sub-component (key post-translational modification) of what was previously considered a single analyte which is important. According to the prior art, 'total' PTX3 is measured. This takes no account of the oligomeric state of the PTX3. Measuring 'total' PTX3 in fact masks the remarkable correlation which the inventors have described, because it does not distinguish the key informational component of the analysis, namely the PTX3 octamers.

Without wishing to be bound by theory, it appears that the tetramer may be an intermediate form between the monomer and the octamer. The invention does not teach a prognostic value for levels of the tetrameric form of PTX3. It may be useful to assess levels of the tetramer in order to "normalise" samples. It appears that levels of the tetramer may be relatively constant. Thus suitably in one embodiment the amounts of octameric PTX3 present may be normalised against the amount of tetrameric PTX3 present. Suitably the amounts of octameric PTX3 present may be expressed as amounts per microgram of tetrameric PTX3. Suitably the determination of octameric PTX3 amounts comprises determination of the amount of octameric PTX3 and determination of the amount of tetrameric PTX3 and calculation of the amount of octameric PTX3 per microgram of tetrameric PTX3.

Suitably the amount of PTX3 octamer is determined.

Suitably the proportion of PTX3 octamer of the total PTX3 is determined.

Suitably the ratio of the octameric PTX3 to the monomeric PTX3 is determined. This has the advantage of not requiring absolute levels of PTX3 to be determined. This has the advantage of avoiding the need to determine the amount of tetrameric PTX3 (or any other uninvolved form of PTX3) present.

Suitably the levels of oxidised PTX3 are assessed.

Suitably the levels of PTX3 octamer are assessed.

Suitably the amount of oxidised PTX3 as a percentage (proportion) of total PTX3 is assessed.

Suitably the amount of PTX3 octamer as a percentage (proportion) of total PTX3 is assessed.

Suitably the ratio of oxidised PTX3 to reduced PTX3 is assessed.

Suitably the ratio of oxidised PTX3 (octameric PTX3) to reduced PTX3 (monomeric PTX3) is assessed.

Suitably the ratio of PTX3 octamer to PTX3 monomer is assessed.

The ratio of octameric PTX3 may be calculated as the ratio of octamer to monomer.

Levels of PTX3 such as levels of monomeric/tetrameric/octameric PTX3 may be assessed by mass spectrometry (MS).

Levels of PTX3 such as levels of monomeric/tetrameric/octameric PTX3 may be assessed by direct readout such as by use of ligand(s) (e.g. antibodies) capable of selectively binding the monomeric/tetrameric/octameric forms of PTX3. Total PTX3 may be quantified using a pan-PTX3 ligand (such as an antibody e.g. an antibody) which binds to all forms of PTX3 regardless of their monomeric/polymeric state.

Use of direct detection of monomeric/tetrameric/octameric PTX3 such as by MS or by selective ligands (e.g. antibodies specific for monomeric/tetrameric/octameric PTX3) offers the advantage of avoiding the need for separation such as gel separation of capillary separation of the monomeric/tetrameric/octameric forms of PTX3, which is required when detecting using a pan-PTX3 ligand for detection (e.g. an antibody which binds PTX3 regardless of its monomeric/tetrameric/octameric state).

It should be noted that the measurement of absolute levels of octameric PTX3 has value in the methods of the invention. However, advantageously it is the proportion of octameric PTX3 which is assessed.

The levels of octameric PTX3 may be visualised via standard characterisation techniques, such as silver staining of electrophoretic gels, measurement of representative peptide ions using mass spectrometry (including multiple reaction monitoring/selected reaction monitoring (MRM/SRM), which is the scan type with the highest duty cycle and is used for monitoring one or more specific ion transition(s) at high sensitivity), or immunological detection methods including Western blotting, enzyme-linked immunosorbent assay (ELISA) or radioimmunoassay. Other such standard characterisation techniques by which levels of octameric PTX3 may be visualised are well known to those skilled in the art. These include successive chromatographic separations of fractions and comparisons of the peaks, capillary electrophoresis, separations using micro-channel networks, including on a micro-chip, and mass spectrometry methods including multiple reaction monitoring (MRM) if appropriate.

Chromatographic separations can be carried out by high performance liquid chromatography as described in Pharmacia literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electroosmotic flow (EOF) of the sample, the positive ions move fastest, followed by uncharged material and negatively charged ions. Thus, proteins are separated essentially according to charge on them.

Micro-channel networks function somewhat like capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20: pages 727-731.

Other methods include performing a binding assay for the PTX3. Any reasonably specific binding agent can be used. Preferably the binding agent is labelled. Preferably the assay is an immunoassay, especially between the biomarker and an antibody that recognises the protein, especially a labelled antibody. It can be an antibody raised against part or all of the marker protein, for example a monoclonal antibody or a polyclonal anti-human antiserum of high specificity for PTX3. The captured PTX3 may then be analysed to determine its monomeric or multimeric state.

Where the binding assay is an immunoassay, it may be carried out by measuring the extent of the PTX3/antibody interaction. Any known method of immunoassay may be used. A sandwich assay is preferred. In an exemplary sandwich assay, a first antibody to the marker protein is bound to the solid phase such as a well of a plastics microtitre plate or blotted membrane, and incubated with the sample and with a labelled second antibody specific to the protein to be assayed. Alternatively, an antibody capture assay can be used. Here, the test sample is allowed to bind to a solid phase, and the anti-PTX3 protein antibody is then added and allowed to bind. After washing away unbound material, the amount of antibody bound to the solid phase is determined using a labelled second antibody, anti- to the first.

The binding agent in the binding assay may be a labelled specific binding agent, which may be an antibody or other specific binding agent. The binding agent will usually be labelled itself, but alternatively it may be detected by a secondary reaction in which a signal is generated, e.g. from another labelled substance.

The label may be an enzyme. The substrate for the enzyme may be, for example, colour-forming, fluorescent or chemiluminescent.

An amplified form of assay may be used, whereby an enhanced "signal" is produced from a relatively low level of protein to be detected. One particular form of amplified immunoassay is enhanced chemiluminescent assay. Conveniently, the antibody is labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

It is also contemplated within the invention to use (i) an antibody array or 'chip', or a bead suspension array capable of detecting PTX3 that interacts with that antibody.

An antibody chip, antibody array or antibody microarray is an array of unique addressable elements on a continuous solid surface whereby at each unique addressable element an antibody with defined specificity for an antigen is immobilised in a manner allowing its subsequent capture of the target antigen and subsequent detection of the extent of such binding. Each unique addressable element is spaced from all other unique addressable elements on the solid surface so that the binding and detection of specific antigens does not interfere with any adjacent such unique addressable element.

A "bead suspension array" is an aqueous suspension of one or more identifiably distinct particles whereby each particle contains coding features relating to its size and colour or fluorescent signature and to which all of the beads of a particular combination of such coding features is coated with an antibody with a defined specificity for an antigen in a manner allowing its subsequent capture of the target antigen and subsequent detection of the extent of such binding. Examples of such arrays can be found at www.luminexcorp.com where application of the xMAP® bead suspension array on the Luminex® 100™ System is described.

Sample

The term "sample" or "biological sample" as used herein means a biological sample derived from a patient to be screened. The biological sample may be any suitable sample known in the art in which the expression of the selected markers can be detected. Included are individual cells or cell populations such as obtained from bodily tissues or fluids. The biological sample may comprise for example a blood or tissue sample.

Suitably the sample may be blood, serum or plasma. Suitably the sample is plasma. Plasma may be prepared from blood by any suitable method known in the art such as centrifugation to remove PBMCs.

Thus suitably the sample for analysis comprises protein.
Suitably the sample is an in vitro sample.
Suitably the sample is an extracorporeal sample.
In one embodiment suitably the method is an in vitro method. In one embodiment suitably the method is an extracorporeal method. In one embodiment suitably the actual sampling of the subject (collection of biological sample) is not part of the method of the invention. Suitably the method does not involve collection of the biological sample. Suitably the sample is a sample previously collected. Suitably the method does not require the presence of the subject whose protein is being assayed. Suitably the sample is an in vitro sample. Suitably the method does not involve the actual medical decision, stricto sensu; such a decision stricto sensu would typically be taken by the physician.

Suitably the method of the invention is conducted in vitro. Suitably the method of the invention is conducted extracorporeally.

When proportions of PTX3 are discussed herein, they are intended to mean a proportion of a mass or estimated total amount of PTX3. For example, eight molecules of PTX3 in a single octameric complex together with eight molecules of PTX3 present as individual monomers gives a ratio of octameric PTX3 to monomeric PTX3 of one to one. It is not a "counting of complexes" approach (i.e. eight molecules of PTX3 present as one octameric complex together with eight molecules of PTX3 present as eight individual monomers does not give a ratio of octameric of PTX3 to monomeric PTX3 of one to eight; the mass of PTX3 present as monomer is equivalent to the mass of PTX3 present as octamer so the ratio is one to one), but it is a counting of the amount of PTX3 present in the alternate forms.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

Further Applications

In another embodiment the invention relates to a method of identifying a subject, such as a subject having sepsis, at risk of developing acute organ failure, comprising performing the method as described above wherein a higher level of octameric PTX3, or ratio of octameric PTX3 to monomeric PTX3, indicates that said subject is identified as at risk of developing acute organ failure.

The invention also relates to method of aiding prediction of clinical outcome in a subject, the method comprising performing the method as described above wherein a higher level of octameric PTX3, or ratio of octameric PTX3 to monomeric PTX3, indicates that said subject is predicted to be a likely non-survivor.

The invention also relates to method of providing a prognosis for a subject, the method comprising performing the method as described above wherein a higher level of octameric PTX3, or ratio of octameric PTX3 to monomeric PTX3, indicates that said subject ascribed a prognosis of probable non-survival.

The invention also relates to a method of treating a subject suffering from an inflammatory disease comprising performing the method as described above wherein if a higher level of octameric PTX3, or ratio of octameric PTX3 to monomeric PTX3, is detected, then a medicament targeting circulating mediators of inflammation is administered to said subject.

Suitably the inflammatory disease is sepsis, most suitably the inflammatory disease is acute organ failure (AOF).

The invention also relates to a method of identifying a subject at risk of death, comprising performing the method as described above wherein a higher level of octameric PTX3, or ratio of octameric PTX3 to monomeric PTX3, indicates that said subject is identified as at risk of death. Death may be because of acute organ failure, sepsis or other inflammatory condition of the invention.

Suitably the invention is applied to ICU patients.

The invention also relates to a method of treating a subject suffering from an inflammatory disease comprising performing the method as described above wherein if a higher level of octameric PTX3, or ratio of octameric PTX3 to monomeric PTX3, is detected, then a medicament targeting inflammation within the tissues is administered to said subject. Suitably the inflammatory disease is sepsis, most suitably the inflammatory disease is acute organ failure (AOF).

We teach a new prognostic biomarker, identified through research, that predicts cardiovascular failure and/or increased risk of death from septic shock. Thus the methods of the invention may be applied to the identification of subjects at risk from cardiovascular failure and/or increased risk of death from septic shock.

In another aspect, the invention relates to a method of collecting information useful in determining the degree of oxidative stress in a subject suffering from an inflammatory disorder, the method comprising providing a sample from said subject and determining the level of octameric PTX3 in said sample, or ratio of octameric PTX3 to monomeric PTX3, wherein a higher level of octameric PTX3, or ratio of octameric PTX3 to monomeric PTX3, indicates a higher degree of oxidative stress.

BRIEF DESCRIPTION OF THE DRAWINGS

Embodiments of the present invention will now be described further, with reference to the accompanying drawings, in which.

EXAMPLES

Figure 1:
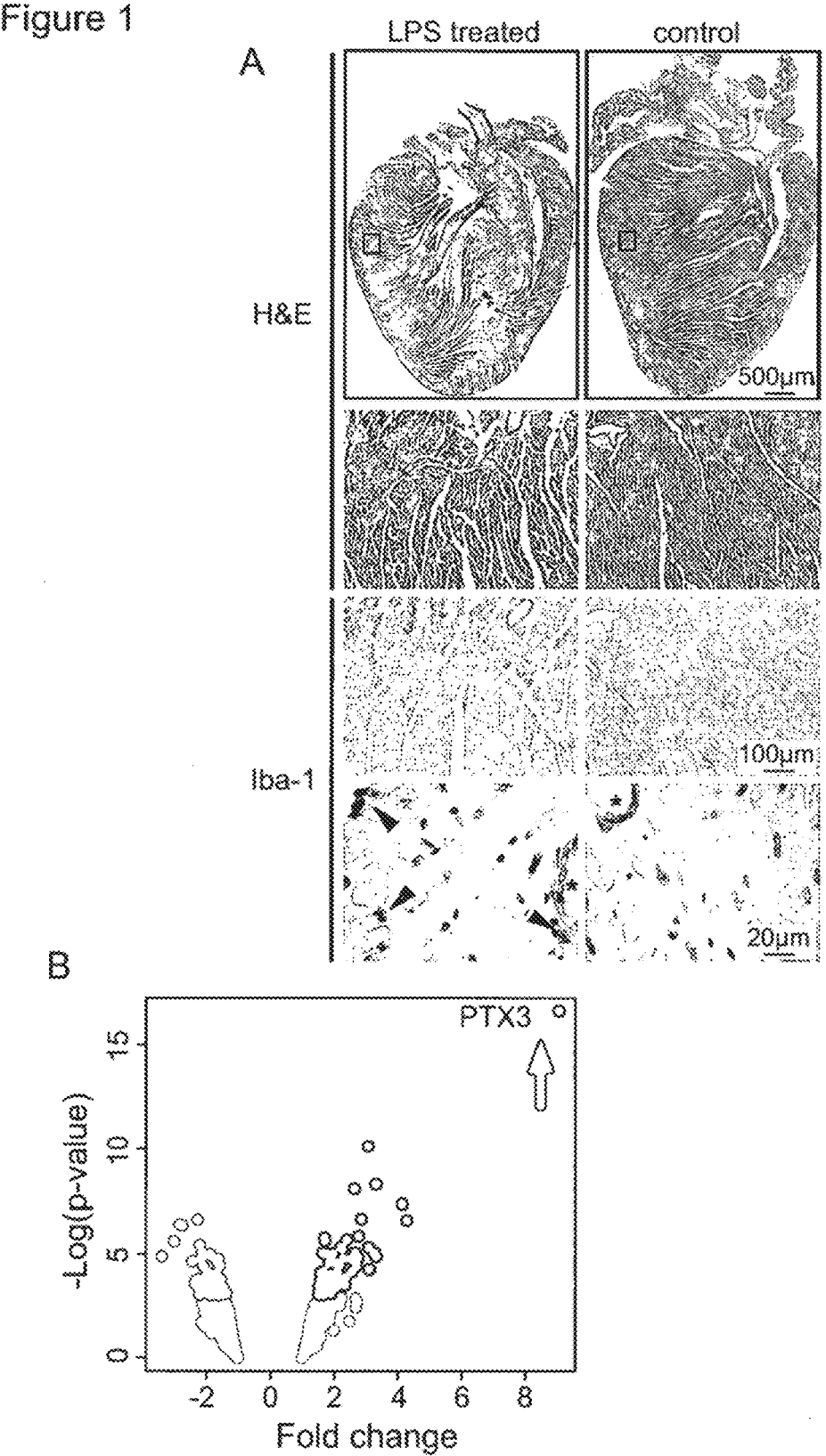
FIG. 1 shows proteomics analysis. A, Hematoxylin and eosin staining in control and septic hearts. Magnification ×10. Scale bar 200 μm. Immunostaining for the macrophage marker 1ba-1. B, Differential expression of extracellular proteins in the proteomic analysis. Note the pronounced upregulation of pentraxin 3 (PTX3, arrow). C, Proteomic spectral count data for PTX3; Cysteine and glycine-rich protein 3 (CSRP3); ankyrin repeat domain-containing protein 1 (ANKR1); and tripartite motif containing protein 72 (Trim72). Equal expression of α-actinin-1 and cardiac myosin-binding protein C (cMyBP-C); D, Validation by immunoblotting. Representative western immunoblots of the Triton-insoluble fraction performed on 4 hearts per group. Probing for α-actinin; cardiac myosin-binding protein C (cMyBP-C); and Coomassie staining assured equal protein loading.
Figure 1:
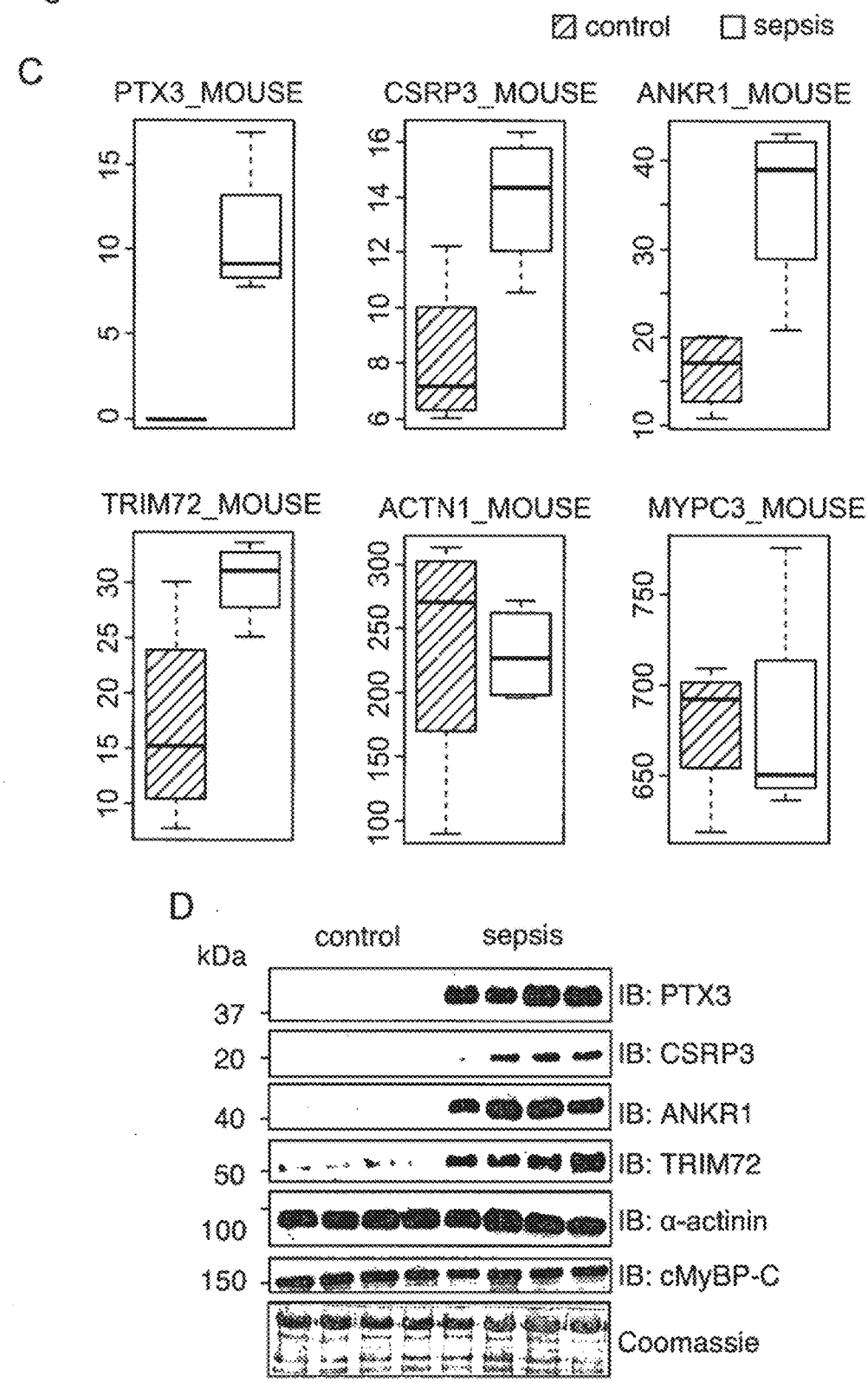

Although illustrative examples of the invention are disclosed in detail herein, with reference to the accompanying drawings, it is understood that the invention is not limited to the precise embodiments disclosed and that various changes and modifications can be effected therein by one skilled in the art without departing from the scope of the invention as defined by the appended claims and their equivalents.

Overview

We have applied a global, tissue-based proteomics approach for biomarker discovery in a mouse model of sepsis. Among the most differentially expressed proteins in cardiac tissue was long pentraxin 3 (PTX3), an acute phase protein that is known to be associated with increased mortality in septic patients. Interestingly, PTX3 accumulated as an octamer due to disulphide-bond formation, most notably in hearts, aortas, kidneys and lungs. Octameric and tetrameric moieties of PTX3 were also detectable in plasma. For the first time, circulating levels of PTX3 monomers, tetramers and octamers were quantified in septic patients (n=31).

Thus, in order to validate our findings, we provide an example of the invention practiced on septic patients in intensive care (ICU). On admission to the intensive care unit, levels of octameric, tetrameric and monomeric PTX3 were determined in all patients. Over a time course of 11 days, reduction of octameric PTX3 to its monomeric form was monitored and found to be associated with a greater survival after 28 days of follow-up. For example, on day 2 post-admission, octameric PTX3 was undetectable in survivors, but still constituted more than half of total PTX3 in non-survivors ($P<0.001$). Levels of tetrameric PTX3 were similar in the two groups. Monomeric PTX3 was inversely associated with cardiac damage markers such as NT-proBNP, high sensitivity troponin I and T.

Thus we demonstrate that, compared to the conventional measurement of total PTX3 in the art, the assessment of the oxidation state of PTX3 provides a superior predictor of disease outcome in septic patients.

Materials and Methods

Materials

Antibodies recognizing pentraxin 3 (PTX3) was from Epitomics, muscle Lim protein (MLP) was a kind gift from Dr Elisabeth Ehler from King's College London, tripartite motif containing protein 72 (TRIM72) was from Aviva Systems Biology, cardiac ankyrin repeat protein (CARP) was from Novus Biologicals, ankyrin repeat and SOCS box protein 2 (ASB2) was from Abcam, α-actinin was from Sigma, cardiac myosin binding-protein C (cMyBP-C) was a kind gift from Prof. Mathias Gautel from King's College London, telethonin was from Santa Cruz Biotechnology, GAPDH conjugated to horseradish peroxidase (HRP) was from Abcam. All other chemicals were from Calbiochem, Invitrogen, Sigma-Aldrich or VWR International, unless otherwise stated. Male C57BL/6J mice were obtained from B&K Universal Ltd.

Animal Models

All experiments were performed in accordance with UK Home Office regulations and the investigation conforms with the Guide for the Care and Use of Laboratory Animals published by the US National Institutes of Health (NIH Publication No. 85-23 revised 1996). C57/BL6 mice were injected with 9 mg/kg Escherichia coli bacterial lipopolysaccharide (LPS; serotype 0.11:B4, Sigma Aldrich, UK) or an equivalent volume of saline and sacrificed 6-8 h later.

Preparation of Tissue Homogenates

Control and septic hearts or other tissues (aorta, kidney, spleen, liver, lung, muscle, brain) were excised and washed briefly in ice-cold Tyrode's solution (pH 7.4) containing in 130 mmol/L NaCl, 5.4 mmol/L KCl, 1.4 mmol/L $MgCl_2$, 0.4 mmol/L $NaH_2PO_4$, 4.2 mmol/L HEPES to remove blood. The tissue was snap-frozen in liquid nitrogen, before homogenization using a motor driven blade 'on ice' in a Tris-based homogenization buffer (pH 7.4) containing 100 mmol/L Tris/HCl, 100 mmol/L EDTA, 100 mmol/L maleimide and protease inhibitors (Roche), at a ratio of 100 mg/ml (10%). Laemmli sample buffer with 10% (3-mercaptoethanol (reducing) or 100 mmol/L maleimide (non-reducing) was added to the tissue homogenates and samples were passed through a narrow gauge needle to shear DNA.

Subfractionation of Mouse Hearts

Mouse heart homogenates were subfractionated into Triton-soluble and Triton-insoluble fractions. Briefly, 1% (v/v) Triton X-100 was added to the mouse heart homogenates and incubated for 15 min on a shaking platform at 4° C. and centrifuged at 13,000 g for 5 min (4° C.). The Triton-soluble fraction was separated from the Triton-insoluble fraction, and non-reducing Laemmli sample buffer was added.

Proteomics Analysis

After separation by SDS-PAGE, silver staining was used for band. To ensure equal loading in each LC-MS/MS experiment, the entire gel lane was excised and subjected to in-gel digestion with trypsin using an Investigator ProGest (Genomic Solutions) robotic digestion system. Tryptic peptides were separated on a nanoflow LC system and eluted with an 80 min gradient (10-25% B in 35 min, 25-40% B in 5 min, 90% B in 10 min and 2% B in 30 min where A=2% ACN, 0.1% formic acid in HPLC H2O and B=90% ACN, 0.1% formic acid in HPLC $H_2O$). The column was coupled to a nanospray source (Picoview). Spectra were collected from an ion-trap mass analyzer (LTQ Orbitrap XL, ThermoFisher Scientific) using full ion scan mode over the mass-to-charge (m/z) range 450-1600. MS/MS was performed on the top six ions in each MS scan using the data-dependent acquisition mode with dynamic exclusion enabled. MS/MS peaklists were generated by extract_msn.exe and matched to mouse database (UniProtKB/Swiss-Prot) using SEQUEST v. 28 (rev. 13), (Bioworks Browser 3.3.1 SP1, ThermoFisher Scientific) and X! Tandem, (Version 2007.01.01.2). Carboxyamidomethylation of cysteine was chosen as fixed modification and oxidation of methionine as variable modification. The mass tolerance was set at 1.5 AMU for the precursor ions and at 1.0 AMU for fragment ions. Two missed cleavages were allowed.

SDS-PAGE and Immunoblot Analysis

SDS-PAGE and immunoblot analysis was carried out as previously described (Haworth et al 2000), using antibodies for total proteins, as indicated. Briefly, protein samples from tissue homogenates, fractionated homogenates or plasma samples in reducing or non-reducing Laemmli sample buffer were separated by 7.5, 10 or 15% SDS-PAGE, transferred to polyvinylidene difluoride (PVDF) membranes and subjected to immunoblotting. Primary antibodies were detected by donkey anti-rabbit or sheep anti-mouse secondary antibodies linked to horseradish peroxidase (HRP; GE Healthcare). Specific protein bands were detected by enhanced chemiluminescence (GE Healthcare) and quantified on a calibrated densitometer (GS-800, BioRad) using Quantity One® 1-D analysis software (v-4.5.1).

Expression and activity of protein kinase D/protein kinase C mu in myocardium: evidence for alpha1-adrenergic receptor- and protein kinase C-mediated regulation.

Haworth R S, Goss M W, Rozengurt E, Avkiran M.

J Mol Cell Cardiol. 2000 June; 32(6):1013-23.

Preparation of Mouse EDTA-Plasma Samples

EDTA plasma was collected from control or LPS-treated mice. The blood samples were centrifuged for 15 min at 2,000 g at 4° C. to deplete cells. The resulting supernatant is plasma. Non-reducing Laemmli sample buffer was added.

Study Design and Setting

This observational cohort study was performed in an 88 bed university hospital general medical-surgical intensive care unit (ICU). The study protocol received ethical approval and written informed consent was obtained either from the patient, if mentally competent, or from their next of kin and consent procedure completed with retrospective consent. The clinical management of the patient was at the discretion of the attending physicians. Consecutive patients meeting the definition for severe sepsis within the first 12 hours following ICU admission between May-October 2011 were included. Severe sepsis was defined as evidence of two or more systemic inflammatory response syndrome (SIRS) criteria, with proven or suspected infection and at least one organ system dysfunction (cardiovascular, respiratory, renal, hematological or metabolic). Exclusion criteria included patients younger than 18 years, those with congenital hypogammaglobulinemia, known protein-losing enteropathies, nephrotic syndrome, neoplastic or proliferative hematological diseases, those having received IVIg therapy in the last 3 months, those receiving high dose steroid therapy, having other ongoing immune dysfunction as defined by the APACHE II co-morbidities, ongoing blood loss (defined by blood transfusion requirement >2 units/24 period) and retroviral disease. Blood samples for Ig and FLC measurements were obtained daily from day 1 (ICU admission) until day 7.

Levy M M, Fink M P, Marshall J C, Abraham E, Angus D, Cook D, Cohen J, Opal S M, Vincent J L, Ramsay G. 2001 sccm/esicm/accp/ats/sis international sepsis definitions conference. Crit Care Med. 2003; 31:1250-1256

Preparation of Human Serum Samples

Whole blood from septic patients was collected at the indicated time-point, The blood was allowed to clot by leaving it undisturbed at room-temperature for 15-30 min. The clot was removed by centrifuging at 2000 g for 10 min at 4° C. Following centrifugation, the serum was immediately transferred into a clean polypropylene tube and stored at −80° C.

Depletion of Serum Albumin from Human Serum

Serum samples were incubated with Blue Sepharose® CL-6B (50 µl per 200 µl serum) at 4° C. for 1 hour on a shaking platform to deplete from serum albumin. Samples were centrifuged at 1000 g for 1 min at 4° C. to remove Blue Sepharose® CL-6B beads, non-reducing Laemmli sample buffer was added and western immunoblot analysis performed.

Enzyme-Linked Immunosorbent Assay (ELISA)

NT-proBNP and hsTnT were determined by the electrochemiluminescence sandwich immunoassay ECLIA on an Elecsys 2010 system (Roche Diagnostics, Germany) in serum samples according to the manufacturers recommendations. The assay range for NT-proBNP was 5-35.000 pg/mL, the assay range for hsTnT was 3-10.000 pg/mL.

hsTnI was determined by a cardiac troponin assay (AR-CHITEKT STAT highly sensitive Troponin I immunoassay, Abbott Diagnostics, USA, ARCHITECT i2000SR). The established limit of detection (LoD) for the assay ranges from 0.8-1.9 with a median of 1.5 pg/mL and an assay range of 0-50.000 pg/mL.

Statistics

Monomeric, tetrameric and octameric PTX3 levels in patients admitted to the ICU were not normally distributed. We therefore used the median and interquartile range to summarize their distributions and used the Wilcoxon rank-sum test to formally test for differences between participants who survived the 28-day follow-up period and those who did not. Analogous methods were used for the biomarkers NT-proBNP hsTnT and hsTnI. Analyses were performed using Stata release 12.1 (StataCorp, College Station, Tex.). Statistical tests were two-sided and used a significance level of $P<0.05$.

Example 1: Proteomics Analysis in a Mouse Model of Sepsis

As a tissue susceptible to sepsis-induced dysfunction, hearts were isolated from control or septic mice 6-8 hours after injection of vehicle saline solution or lipopolysaccharide (LPS; 9 mg/kg ip). Tissue sections were stained with hematoxylin and eosin. A representative microscopic image is shown in FIG. 1A (upper panel). Macrophage infiltration was detected by immunostaining within 6-8 hours after injection (lower panel). The cardiac proteome (n=4 per group) was subfractionated based on protein solubility in 1% Triton. The Triton-insoluble fraction was separated by SDS-PAGE; the entire lane was divided into a series of gel bands; and proteomic analysis was performed on each of them with a high-mass-accuracy tandem mass spectrometer (LTQ Orbitrap XL, ThermoFisher Scientific).

Differentially expressed proteins are highlighted in Table 1.

TABLE 1

Differential protein expression in septic hearts. Hearts from control or LPS-treated C57Bl6 mice were fractionated using 1% Triton X-100, separated on a 1D gel and identified by LC-MS/MS. Abundance was estimated based on the normalized spectral count. A cutoff of a 1.5-fold enrichment or −1.5-fold reduction was used (see FIG. 1B).

| Uniprot | Location | logFC | AveExpr | t | P-Value |
|---|---|---|---|---|---|
| Upregulated | | | | | |
| PTX3_MOUSE | Pentraxin 3 | 9.063029 | 1.921067 | 12.24959 | 6.03E−08 |
| ITIH2_MOUSE | Inter-alpha-trypsin inhibitor heavy chain H2 | 4.28346 | 1.380459 | 4.180585 | 0.001398 |
| IIGP1_MOUSE | Interferon-inducible GTPase 1 | 4.141988 | 2.945678 | 4.629279 | 0.00065 |
| ABRA_MOUSE | Actin-binding Rho-activating protein | 3.320944 | 1.196867 | 3.208899 | 0.007899 |
| RT34_MOUSE | 28S ribosomal protein S34, mitochondrial | 3.316714 | 1.58304 | 5.213508 | 0.00025 |
| GBP5_MOUSE | Guanylate-binding protein 5 | 3.275107 | 1.405463 | 3.299435 | 0.006701 |
| SPA3N_MOUSE | Serine protease inhibitor A3N | 3.113453 | 1.150328 | 2.870257 | 0.014639 |

TABLE 1-continued

Differential protein expression in septic hearts. Hearts from control or LPS-treated C57Bl6 mice were fractionated using 1% Triton X-100, separated on a 1D gel and identified by LC-MS/MS. Abundance was estimated based on the normalized spectral count. A cutoff of a 1.5-fold enrichment or −1.5-fold reduction was used (see FIG. 1B).

| Uniprot | Location | logFC | AveExpr | t | P-Value |
|---|---|---|---|---|---|
| RALB_MOUSE | Ras-related protein Ral-B | 3.10062 | 1.147349 | 3.447412 | 0.005127 |
| SLFN5_MOUSE | Schlafen family member 5 | 3.084478 | 1.240669 | 6.422555 | 4.02E−05 |
| ICAM1_MOUSE | Intercellular adhesion molecule 1 | 2.864525 | 1.090218 | 4.216975 | 0.001313 |
| GBP2_MOUSE | Interferon-induced guanylate-binding protein 2 | 2.775832 | 2.204718 | 3.742521 | 0.00302 |
| IBP7_MOUSE | Insulin-like growth factor-binding protein 7 | 2.757344 | 1.256881 | 3.169481 | 0.008486 |
| PPIB_MOUSE | Peptidyl-prolyl cis-trans isomerase B | 2.713455 | 1.346745 | 2.967725 | 0.012255 |
| PYGB_MOUSE | Glycogen phosphorylase, brain form | 2.673938 | 3.139724 | 3.315755 | 0.006506 |
| PDIA3_MOUSE | Protein disulfide-isomerase A3 | 2.647987 | 3.211363 | 5.075254 | 0.000312 |
| PERM_MOUSE | Myeloperoxidase | 2.572686 | 1.206879 | 2.809469 | 0.016354 |
| CRIP2_MOUSE | Cysteine-rich protein 2 | 2.528019 | 2.666509 | 3.143685 | 0.008894 |
| HBB1_MOUSE | Hemoglobin subunit beta-1 | 2.40557 | 3.221641 | 3.65205 | 0.003549 |
| SYWC_MOUSE | Tryptophan--tRNA ligase, cytoplasmic | 2.372679 | 1.717561 | 2.656368 | 0.021608 |
| DDX3Y_MOUSE | ATP-dependent RNA helicase DDX3Y | 2.350304 | 2.446327 | 2.456994 | 0.031001 |
| DNJC7_MOUSE | DnaJ homolog subfamily C member 7 | 2.292453 | 1.633601 | 3.159826 | 0.008636 |
| SFRS3_MOUSE | Serine/arginine-rich splicing factor 3 | 2.26317 | 2.322341 | 3.422948 | 0.005359 |
| C560_MOUSE | Succinate dehydrogenase cytochrome b560 subunit, mitochondrial | 2.219717 | 2.305071 | 3.443866 | 0.00516 |
| GLGB_MOUSE | 1,4-alpha-glucan-branching enzyme | 2.169217 | 1.317813 | 2.977512 | 0.012038 |
| GSTP1_MOUSE | Glutathione S-transferase P1 | 2.13899 | 1.093613 | 2.597789 | 0.024033 |
| PPAC_MOUSE | Low molecular weight phosphotyrosine protein phosphatase | 2.112521 | 0.870553 | 2.838255 | 0.015518 |
| TPPC9_MOUSE | Trafficking protein particle complex subunit 9 | 2.079614 | 0.956314 | 2.393772 | 0.034736 |
| GDIA_MOUSE | Rab GDP dissociation inhibitor alpha | 2.022528 | 1.463353 | 2.672549 | 0.020982 |
| PLSB_MOUSE | Glycerol-3-phosphate acyltransferase 1, mitochondrial | 2.008347 | 1.048152 | 2.573757 | 0.025103 |
| TBB2A_MOUSE | Tubulin beta-2A chain | 1.986439 | 1.547451 | 3.064915 | 0.010265 |
| BAT3_MOUSE | Large proline-rich protein BAG6 | 1.973505 | 1.13254 | 2.492477 | 0.029079 |
| SIRT2_MOUSE | NAD-dependent protein deacetylase sirtuin-2 | 1.968192 | 1.920829 | 3.285651 | 0.006871 |
| ANKR1_MOUSE | Ankyrin repeat domain-containing protein 1 | 1.914626 | 4.458796 | 3.068766 | 0.010194 |
| CC90A_MOUSE | Coiled-coil domain-containing protein 90A, mitochondrial | 1.905284 | 2.543981 | 2.224303 | 0.047014 |
| RAD_MOUSE | GTP-binding protein RAD | 1.887582 | 2.355275 | 2.74624 | 0.01835 |
| TRI72_MOUSE | Tripartite motif-containing protein 72 | 1.883336 | 4.389895 | 2.631353 | 0.022613 |
| PYGM_MOUSE | Glycogen phosphorylase, muscle form | 1.851731 | 3.856654 | 3.039272 | 0.010757 |
| MVP_MOUSE | Major vault protein | 1.802701 | 2.639078 | 2.540931 | 0.02664 |
| RALA_MOUSE | Ras-related protein Ral-A | 1.794168 | 1.359501 | 2.252158 | 0.044744 |
| LEG1_MOUSE | Galectin-1 | 1.794033 | 2.895016 | 2.700122 | 0.019956 |
| CSRP3_MOUSE | Cysteine and glycine-rich protein 3 | 1.752936 | 3.495756 | 3.279577 | 0.006947 |
| HNRDL_MOUSE | Heterogeneous nuclear ribonucleoprotein D-like | 1.74135 | 1.857464 | 2.442683 | 0.031811 |
| ATPB_MOUSE | ATP synthase subunit beta, mitochondrial | 1.715768 | 7.570634 | 3.631231 | 0.003684 |
| ATPO_MOUSE | ATP synthase subunit O, mitochondrial | 1.699623 | 5.352927 | 3.697727 | 0.003271 |
| THIO_MOUSE | Branched-chain alpha-keto acid dehydrogenase complex component E2 | 1.688882 | 1.724717 | 2.294025 | 0.041528 |
| ODB2_MOUSE | Lipoamide acyltransferase component of branched-chain alpha-keto acid dehydrogenase complex, mitochondrial | 1.661322 | 3.602847 | 2.821139 | 0.01601 |
| PP1B_MOUSE | Serine/threonine-protein phosphatase PP1-beta catalytic subunit | 1.658211 | 3.791152 | 2.193562 | 0.049646 |
| RAB2A_MOUSE | Ras-related protein Rab-2A | 1.648191 | 2.781973 | 2.47408 | 0.03006 |
| RU2A_MOUSE | U2 small nuclear ribonucleoprotein A' | 1.647417 | 2.387071 | 2.293241 | 0.041586 |
| CH60_MOUSE | 60 kDa heat shock protein, mitochondrial | 1.644238 | 4.490451 | 3.30482 | 0.006636 |
| CC001_MOUSE | Translocase of inner mitochondrial membrane domain-containing protein 1 | 1.642665 | 2.576589 | 2.528974 | 0.027222 |
| ELAV1_MOUSE | ELAV-like protein 1 | 1.62906 | 3.386151 | 2.405814 | 0.033993 |
| RL36_MOUSE | 60S ribosomal protein L36 | 1.625145 | 2.176585 | 2.568856 | 0.025327 |
| AAKG1_MOUSE | 5'-AMP-activated protein kinase subunit gamma-1 | 1.620434 | 2.57841 | 2.301968 | 0.040944 |
| HSPB1_MOUSE | Heat shock protein beta-1 | 1.608841 | 3.561607 | 2.359591 | 0.036933 |
| EHD2_MOUSE | EH domain-containing protein 2 | 1.584704 | 3.329925 | 2.777656 | 0.01733 |
| TMM65_MOUSE | Transmembrane protein 65 | 1.562512 | 2.428869 | 2.563244 | 0.025585 |
| RRFM_MOUSE | Ribosome-recycling factor, mitochondrial | 1.544207 | 2.059405 | 2.219951 | 0.047378 |
| DCTN4_MOUSE | Dynactin subunit 4 | 1.535688 | 2.547558 | 2.43364 | 0.032333 |
| ODO2_MOUSE | 2-oxoglutarate dehydrogenase complex component E2 | 1.522302 | 4.143902 | 2.244968 | 0.04532 |
| TBA1B_MOUSE (+1) | Tubulin alpha-1B chain | 1.51676 | 3.803447 | 2.200976 | 0.048999 |
| Downregulated | | | | | |
| HCC1_MOUSE | SAP domain-containing ribonucleoprotein | −1.54265 | 2.859529 | −2.62194 | 0.023002 |
| RLA2_MOUSE | 60S acidic ribosomal protein P2 | −1.58225 | 3.870575 | −2.98175 | 0.011946 |
| AKAP1_MOUSE | A-kinase anchor protein 1, mitochondrial | −1.60944 | 3.02377 | −2.30987 | 0.04037 |
| KAP0_MOUSE | cAMP-dependent protein kinase type I-alpha regulatory subunit | −1.61537 | 3.340021 | −2.19376 | 0.049629 |
| PURA_MOUSE | Transcriptional activator protein Pur-alpha | −1.61727 | 2.080311 | −2.54321 | 0.02653 |
| RS17_MOUSE | 40S ribosomal protein S17 | −1.62322 | 3.544121 | −3.16273 | 0.008591 |
| YBOX1_MOUSE | Nuclease-sensitive element-binding protein 1 | −1.65283 | 4.09328 | −3.05528 | 0.010447 |

TABLE 1-continued

Differential protein expression in septic hearts. Hearts from control or LPS-treated C57Bl6 mice were fractionated using 1% Triton X-100, separated on a 1D gel and identified by LC-MS/MS. Abundance was estimated based on the normalized spectral count. A cutoff of a 1.5-fold enrichment or −1.5-fold reduction was used (see FIG. 1B).

| Uniprot | Location | logFC | AveExpr | t | P-Value |
|---|---|---|---|---|---|
| COFA1_MOUSE | Collagen alpha-1(XV) chain | −1.66057 | 4.313515 | −2.72665 | 0.019016 |
| PRDBP_MOUSE | Protein kinase C delta-binding protein | −1.66488 | 2.765078 | −2.60061 | 0.02391 |
| SRPK2_MOUSE | SRSF protein kinase 2 | −1.66611 | 2.428824 | −2.79548 | 0.016776 |
| DNJA4_MOUSE | DnaJ homolog subfamily A member 4 | −1.67244 | 2.993511 | −2.55846 | 0.025808 |
| MLRA_MOUSE | Myosin regulatory light chain 2, atrial isoform | −1.68896 | 3.041863 | −2.41781 | 0.033267 |
| CHCH6_MOUSE | Coiled-coil-helix-coiled-coil-helix domain-containing protein 6, mitochondrial | −1.71979 | 2.264609 | −2.40108 | 0.034283 |
| HXK2_MOUSE | Hexokinase-2 | −1.74597 | 4.863042 | −2.74344 | 0.018444 |
| PGM2_MOUSE | Phosphoglucomutase-2 | −1.75201 | 2.171081 | −2.46438 | 0.030591 |
| DNJA2_MOUSE | DnaJ homolog subfamily A member 2 | −1.77878 | 2.470372 | −2.42178 | 0.033031 |
| PRS7_MOUSE | 26S protease regulatory subunit 7 | −1.80484 | 2.23257 | −2.2631 | 0.043881 |
| MLF1_MOUSE | Myeloid leukemia factor 1 | −1.83893 | 1.953055 | −2.32926 | 0.038995 |
| RS26_MOUSE | 40S ribosomal protein S26 | −1.85861 | 2.687074 | −3.24474 | 0.007401 |
| DUS28_MOUSE | Dual specificity phosphatase 28 | −1.8606 | 1.927575 | −2.60552 | 0.023698 |
| DAG1_MOUSE | Dystroglycan | −1.86378 | 2.593578 | −2.19671 | 0.04937 |
| CDIPT_MOUSE | CDP-diacylglycerol--inositol 3-phosphatidyltransferase | −1.87217 | 1.750954 | −3.28279 | 0.006907 |
| NDUV3_MOUSE | NADH dehydrogenase [ubiquinone] flavoprotein 3, mitochondrial | −1.88956 | 2.536157 | −2.50173 | 0.028597 |
| ACAP2_MOUSE | Arf-GAP with coiled-coil, ANK repeat and PH domain-containing protein 2 | −1.96254 | 1.178296 | −2.27197 | 0.043193 |
| SNX2_MOUSE | Sorting nexin-2 | −1.97113 | 2.207351 | −2.7913 | 0.016904 |
| ZN294_MOUSE | E3 ubiquitin-protein ligase listerin | −1.97605 | 1.634662 | −2.72192 | 0.01918 |
| TM201_MOUSE | Transmembrane protein 201 | −1.98226 | 2.204376 | −2.74916 | 0.018253 |
| TOP3B_MOUSE | DNA topoisomerase 3-beta-1 | −1.98359 | 1.526997 | −2.31034 | 0.040336 |
| SMTN_MOUSE | Smoothelin | −1.98701 | 2.778145 | −2.2469 | 0.045164 |
| TXLNB_MOUSE | Beta-taxilin | −2.00704 | 2.889618 | −2.64548 | 0.02204 |
| DAAM1_MOUSE | Disheveled-associated activator of morphogenesis 1 | −2.03408 | 1.57191 | −2.6175 | 0.023189 |
| DYHC1_MOUSE | Cytoplasmic dynein 1 heavy chain 1 | −2.0515 | 1.136713 | −2.44338 | 0.031771 |
| PLAP_MOUSE | Phospholipase A-2-activating protein | −2.09866 | 1.11626 | −2.96048 | 0.012418 |
| K0774_MOUSE | Microtubule-associated tumor suppressor candidate 2 homolog | −2.11729 | 1.940026 | −2.43367 | 0.032331 |
| BZW2_MOUSE | Basic leucine zipper and W2 domain-containing protein 2 | −2.13847 | 2.000364 | −3.31545 | 0.00651 |
| ARP2_MOUSE | Actin-related protein 2 | −2.14339 | 3.164004 | −3.18823 | 0.008201 |
| EFTS_MOUSE | Elongation factor Ts, mitochondrial | −2.18372 | 0.950261 | −3.1338 | 0.009055 |
| VWA1_MOUSE | von Willebrand factor A domain-containing protein 1 | −2.21693 | 2.279927 | −3.52397 | 0.004466 |
| MTA1_MOUSE | Metastasis-associated protein MTA1 | −2.21815 | 2.377727 | −2.34397 | 0.037982 |
| EIF3I_MOUSE | Eukaryotic translation initiation factor 3 subunit I | −2.22458 | 2.134371 | −2.6169 | 0.023214 |
| THOP1_MOUSE | Thimet oligopeptidase | −2.22799 | 2.42128 | −2.20749 | 0.048436 |
| DRG1_MOUSE | Developmentally-regulated GTP-binding protein 1 | −2.28186 | 2.996228 | −4.211 | 0.001326 |
| PKHA6_MOUSE | Pleckstrin homology domain-containing family A member 6 | −2.33883 | 2.720331 | −2.59509 | 0.02415 |
| CA077_MOUSE | Friend of PRMT1 protein | −2.35968 | 1.618213 | −2.50869 | 0.028239 |
| RHEB_MOUSE | GTP-binding protein Rheb | −2.45239 | 1.861274 | −3.09452 | 0.009726 |
| EEPD1_MOUSE | Endonuclease/exonuclease/phosphatase family domain-containing protein 1 | −2.76507 | 0.906446 | −4.05579 | 0.001737 |
| MTUS1_MOUSE | Microtubule-associated tumor suppressor 1 homolog | −2.85345 | 2.091359 | −4.07352 | 0.001684 |
| ASB2_MOUSE | Ankyrin repeat and SOCS box protein 2 | −3.02373 | 1.919678 | −3.61828 | 0.00377 |
| 5NTD_MOUSE | 5'-nucleotidase | −3.41014 | 2.035405 | −3.22299 | 0.007699 |

The most pronounced change after LPS injection was observed for long pentraxin 3 (FIG. 1B, PTX3; fold change 9.06, p-value=6.03 E-08), an acute phase glycoprotein, secreted by a variety of cells and tissues in response to pro-inflammatory cytokines,[8] followed by inter-alpha-trypsin inhibitor heavy chain H2 (ITIH2_MOUSE; fold change 4.28; p-value=0.001), a known PTX3 ligand.

Example 2: Validation by Immunoblotting

Immunoblotting was performed for independent confirmation of the proteomics data (FIG. 1C). The Western blots demonstrated a marked increase of PTX3 in the Triton-insoluble mouse heart extracts under septic conditions (FIG. 1D). Furthermore, differences of intracellular proteins, such as muscle Lim protein (MLP), tripartite motif containing protein 72 (TRIM72) and cardiac ankyrin repeat protein (CARP), were confirmed. Equal protein loading was demonstrated by immunoblotting for α-actinin and cardiac myosin-binding protein C (cMyBP-C) and Coomassie staining.

Example 3: Oxidation State of PTX3

The identification of PTX3 in the Triton-insoluble fraction was unexpected. Extracellular proteins should get solubilized by 1% Triton. It was therefore very surprising when this observation was made.

PTX3 belongs to the pentraxin superfamily. Secreted PTX3 can bind to pathogens to induce classical complement activation. Notably, oligomerisation of PTX3 into tetrameric and octameric complexes via interprotein disulphide bond formation through adjacent cysteine residues in PTX3 monomer subunits was described as a prerequisite for its biological activity.[9]

Figure 2:
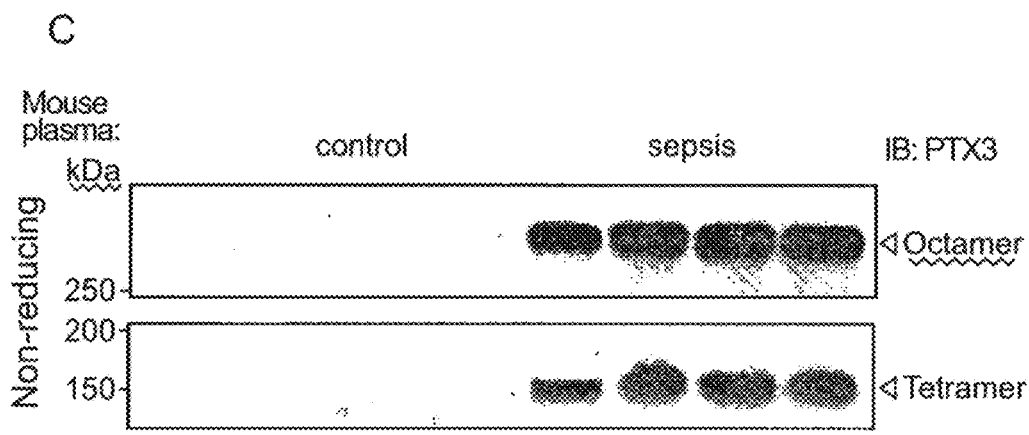
FIG. 2 shows PTX3 oxidation in sepsis. A, Hearts from control C57B16 or LPS-treated mice were subfractionated into Triton-soluble and insoluble fraction. Fractions were subjected to western immunoblot analysis under reducing (upper panel) or non-reducing conditions (bottom panel). Representative western immunoblots from 3 mouse hearts per group were probed for PTX3, telethonin, (marker of the insoluble myofilament containing compartment) and GAPDH (marker of the soluble cytosol containing compartment). The different oxidation states of PTX3 (octamer, tetramer and monomer) were analysed by immunostaining. B, Tissue samples from heart, aorta, kidney, spleen, liver, lung, muscle and brain were subjected to western immunoblot analysis under non-reducing (upper panel) or reducing (bottom panel) gel conditions and probed with a PTX3 antibody. C, Plasma samples from control C57B16 mice or from mice after LPS-induced sepsis were depleted of albumin and analysed for PTX3 protein content and oxidation state using western immunoblot analysis under non-reducing conditions. The representative western immunoblot displays the results of 4 mice per group.

To further investigate the enrichment of PTX3 in the cardiac proteome, the Triton-soluble and Triton-insoluble fractions (n=3 per group) of hearts harvested 6-8 hours post LPS injection were compared under reducing and non-reducing conditions. The effectiveness of the subfractionation procedure by 1% Triton was confirmed by immunoblotting for selected markers of different cardiomyocyte compartments, glyceraldehyde-3-phosphate dehydrogenase (GAPDH; cytosolic) and telethonin (particulate/myofilament) (FIG. 2A). Under reducing conditions, PTX3 was clearly detectable as a 45 kDa moiety in sepsis hearts.

N-linked glycosylation accounts for a 5 kDa shift of PTX3 with a predicted molecular mass for the reduced protein of 40 kDa.[10]

Immunoblot analysis performed under non-denaturing conditions revealed that PTX3 forms high molecular weight complexes resulting in the formation of tetramers (180 kDa) and octamers (360 kDa) (FIG. 2A).

While both the tetramer and the octamer were present in the Triton-soluble fraction, only the octamer was detected in the Triton-insoluble fraction of sepsis hearts.

Example 4: Tissue Distribution of Oxidised PTX3

Tissue homogenates from aorta, kidney, spleen, liver, lung, muscle and brain from control or septic mice were sampled under reducing or non-reducing conditions (FIG. 2B). Increased PTX3 octamer levels were detectable in heart, aorta, lung and kidney from septic mice. The high molecular weight PTX3 moieties were converted to monomers under reducing conditions. In contrast, no PTX3 protein was detectable in tissue homogenates of control mice.

Notably, tetrameric and octameric moieties of PTX3 were also detectable in plasma of septic mice (FIG. 2C). This demonstrates that samples comprising or derived from blood (serum), such as samples comprising plasma, are useful in the operation of the invention.

Example 5: Circulating Oxidised PTX3 in Sepsis Patients

Octameric, tetrameric and monomeric PTX3 levels were quantified in deteriorating septic ward patients (n=31) referred to ICU Outreach Teams, without established AOF. Their clinical characteristics are shown in Table 2.

TABLE 2

| | Clinical Characteristics of Sepsis Patients | | | |
|---|---|---|---|---|
| Variable | Entire Study cohort (n = 31) | 28 day Survivors (n = 23) | 28 day Non-Survivors (n = 8) | p-value |
| Age (years) | 67.4 (11.9) | 66.0 (12.2) | 71.0 (12.8) | 0.29 |
| Male:Female | 19:12 (61.3%:38.3%) | 15:8 (65.3%:34.7%) | 4:4 (50.0%:50.0%) | 0.45 |
| APACHE II Score | 20.6 (6.0) | 19.3 (6.1) | 24.4 (3.7) | 0.03 |
| Medical:Surgical | 26:5 (83.8%:16.1%) | 18:5 (78.3%:21.7%) | 8 (100%) | 0.20 |
| WCC count | 13.5 (1.3, 49.1) | 11.3 (1.3, 25.8) | 17.8 (11.8, 49.1) | 0.04 |
| Neutrophil count | 11.8 (1.1, 45.2) | 9.8 (1.1, 23.3) | 16.3 (9.8, 45.2) | 0.03 |
| Lymphocyte count | 0.55 (0.1, 3.9) | 0.7 (0.1, 3.9) | 0.45 (0.2, 1.5) | 0.15 |
| CRP | 130 (8, 429) | 143 (8, 429) | 115 (29, 148) | 0.13 |
| Respiratory SOFA | 3 (2, 4) | 3 (2, 4) | 4 (3, 4) | 0.03 |
| CVS SOFA | 4 (0, 4) | 4 (0, 4) | 4 (0, 4) | 0.47 |
| Renal SOFA | 1 (0, 4) | 1 (0, 4) | 0 (0, 4) | 0.50 |
| Hepatic SOFA | 0 (0, 2) | 0 (0, 2) | 0 (0, 0) | 0.33 |
| Coagulation SOFA | 0 (0, 4) | 0 (0, 4) | 0 (0, 3) | 0.51 |
| Neurological SOFA | 0 (0, 3) | 0 (0, 3) | 0 (0, 0) | 0.55 |
| t-SOFA score | 8 (4, 12) | 8 (2, 14) | 8 (3, 13) | 0.98 |
| ICU LOS (days) | 9.9 (5.7) | 9.5 (6.3) | 11 (3.5) | 0.23 |
| Hospital LOS (days) | 23 (4, 216) | 30 (7, 216) | 11 (4, 18) | 0.001 |

Serum samples were taken in a longitudinal manner at 8 different time points: on the day of admission to ICU (day 0), at days 1 to 6 and at day 11.

Immunoblot analysis was performed under non-reducing conditions.

Figure 3:
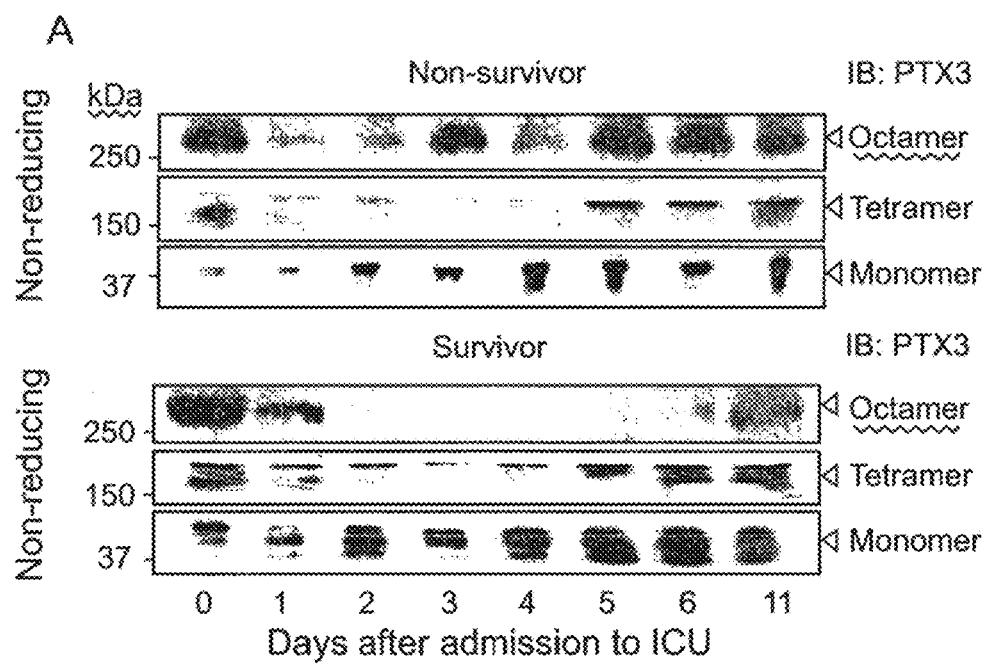
FIG. 3 shows association of PTX3 oxidation with survival. A, Serum samples from 31 septic patients after admission to ICU (day 0) over a time course of 11 days were analysed for PTX3 plasma levels after albumin depletion. The western immunoblots are representative examples of the development of the PTX3 oxidation state with time after admission in a non-surviving sepsis patient (upper panel) compared to a surviving sepsis patient (bottom panel). B, Monomeric, tetrameric and octameric PTX3 levels were quantified for each patient and time point using western immunoblot analysis performed under non-reducing conditions. * denotes statistical significant difference between patients who died and those who survived during follow-up; $P<0.05$. C, Comparison of PTX3 oxidation levels between survivors and non-survivors on day 2 post admission to ICU.
Figure 3:
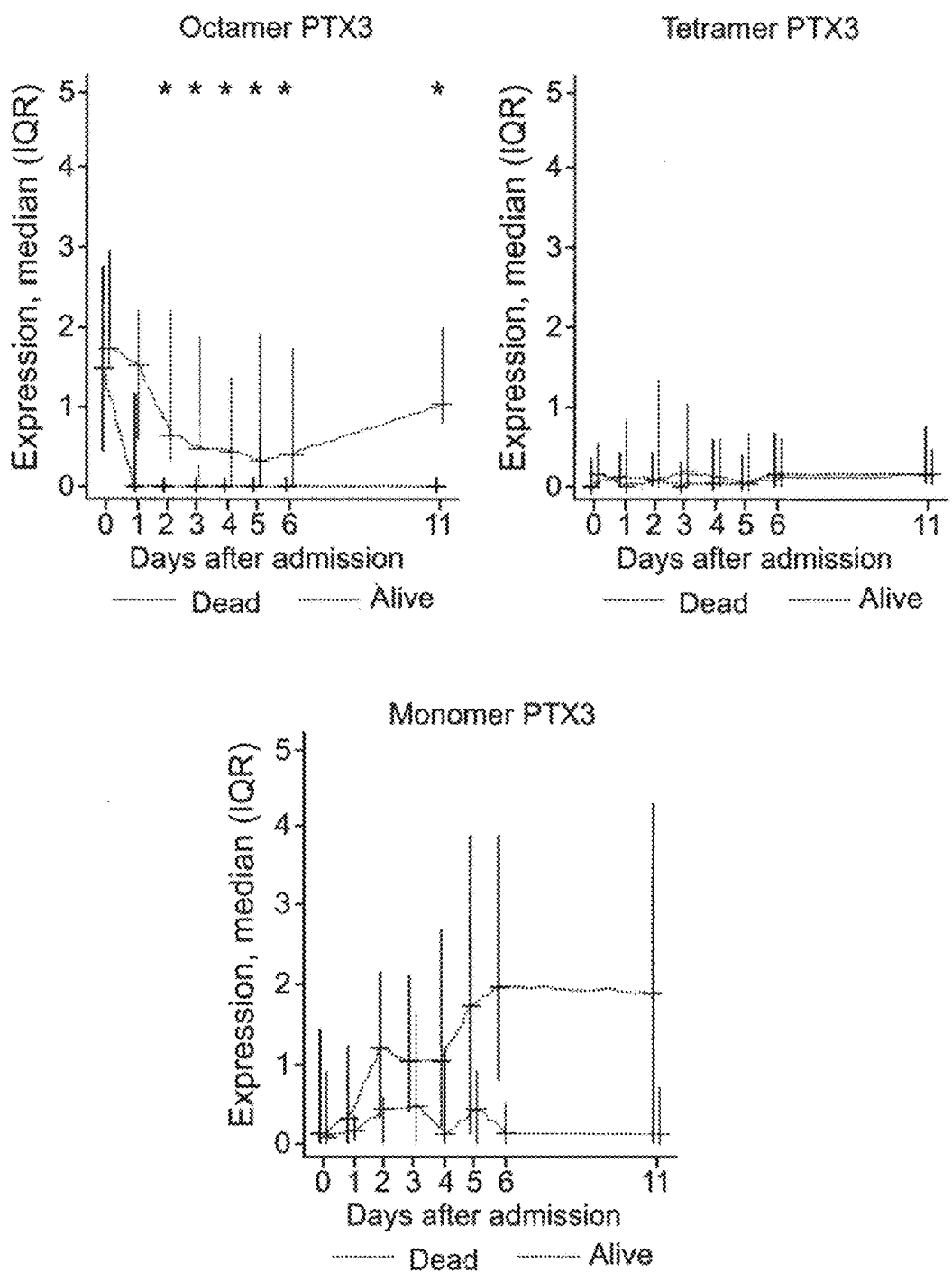
Figure 3:
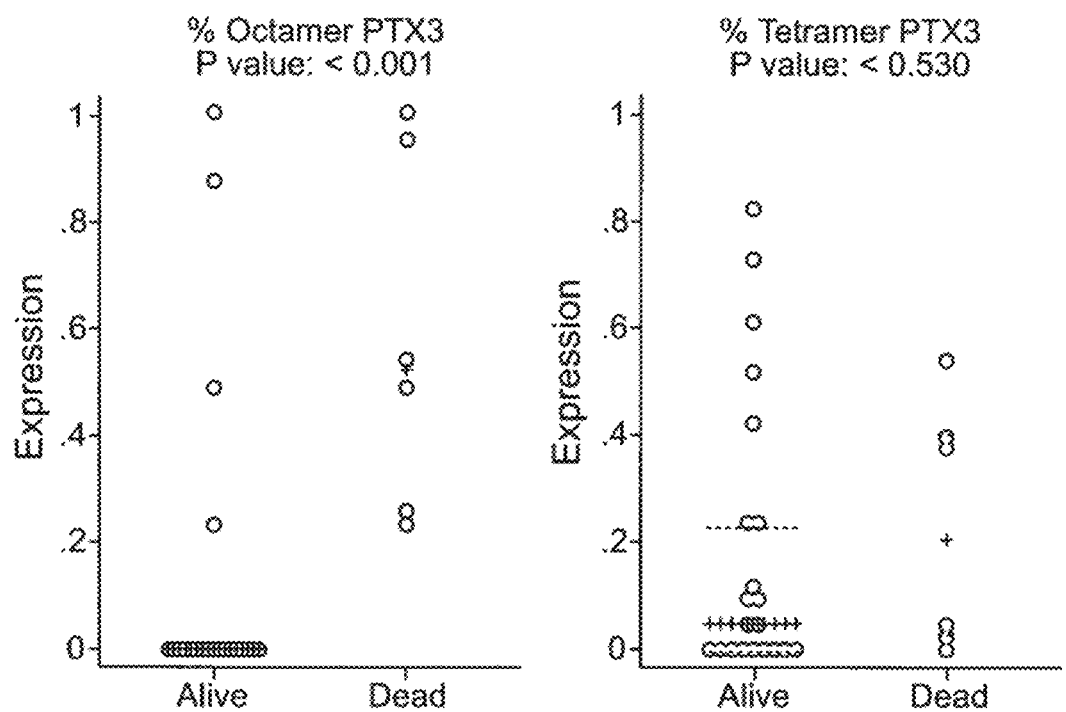
Figure 3:
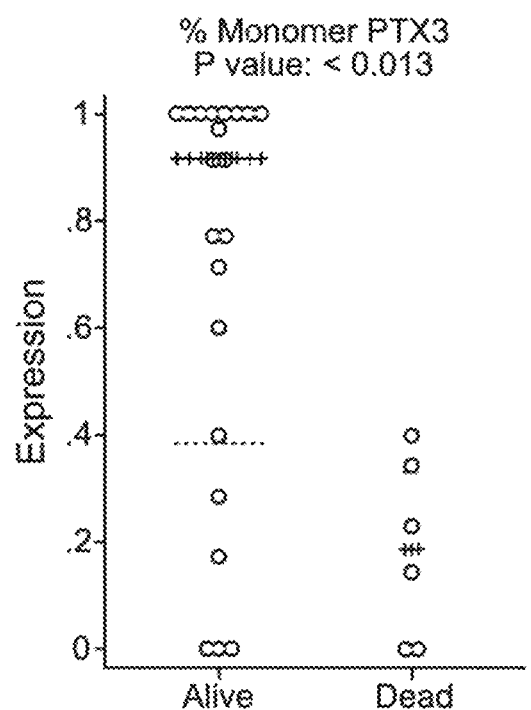

The levels of the different oxidized PTX3 moieties were correlated with the survival of patients (FIG. 3A). On day 0, there was no difference in octameric, tetrameric and monomeric PTX3 levels between survivors and non-survivors. Over the time course of 11 days, however, a reduction of octameric to monomeric PTX3 was associated with a greater survival during 28 days follow-up (FIG. 3B). By day 2 post admission, PTX3 oxidation predicted adverse clinical outcome: Octameric PTX3 was undetectable in to survivors, but constituted more than 50% of total PTX3 in non-survivors (p<0.001, FIG. 3C). On the other hand, monomeric PTX3 constituted 90% of total PTX3 in survivors, but only 20% in non-survivors (p<0.013).

There was no significant difference in tetrameric PTX3 between survivors and non-survivors.

Figure 4:
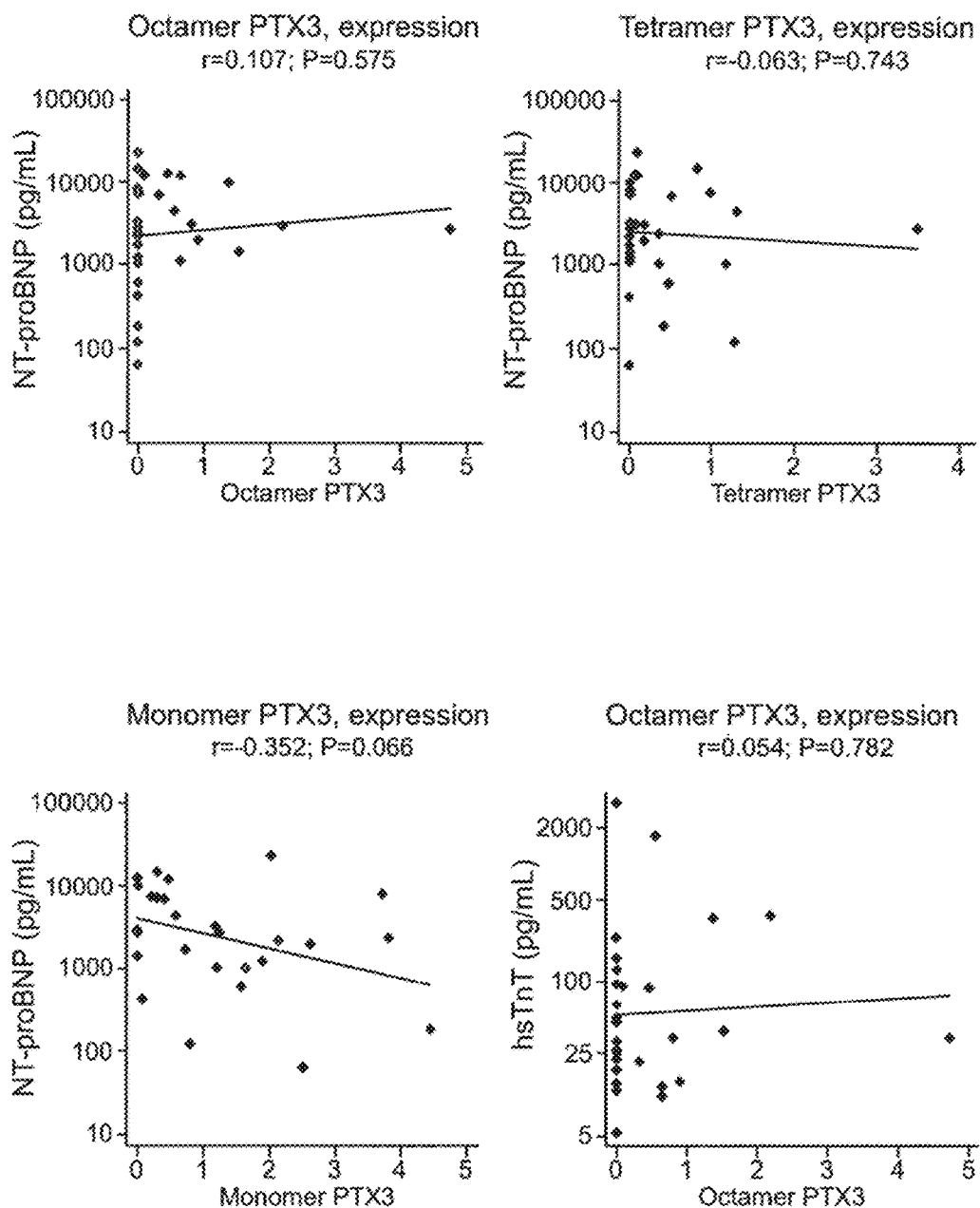
FIG. 4 shows association of PTX3 oxidation with cardiac damage markers. A, Correlation of octamer, tetramer and monomer levels of PTX3 with NT-proBNP (upper panel), hsTnT (middle panel), and hsTnI (bottom panel). B, Comparison of NT-proBNP, hsTnT, and hsTnI levels between survivors and non-survivors on day 2 post admission to ICU.
Figure 4:
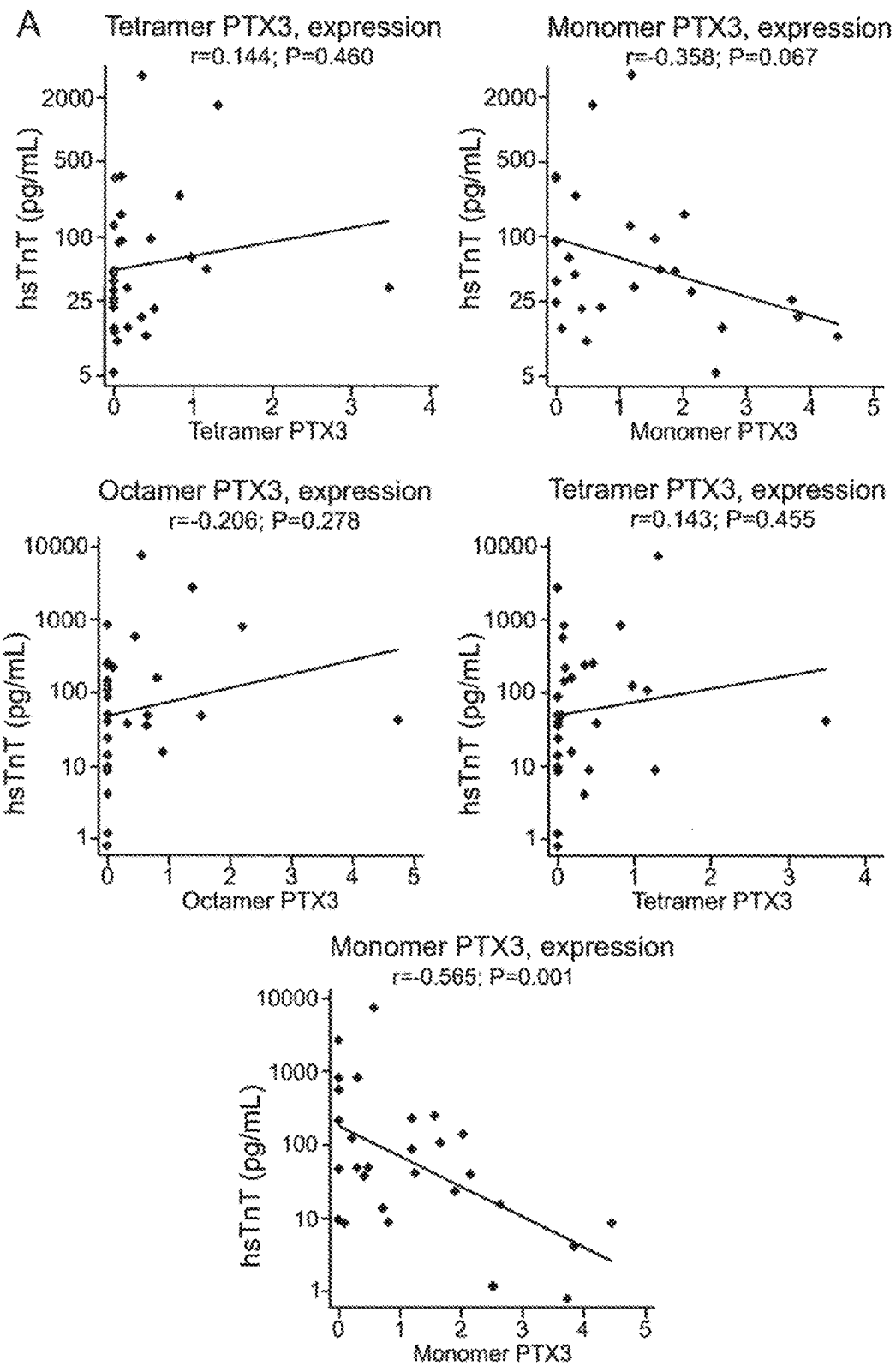
Figure 4:
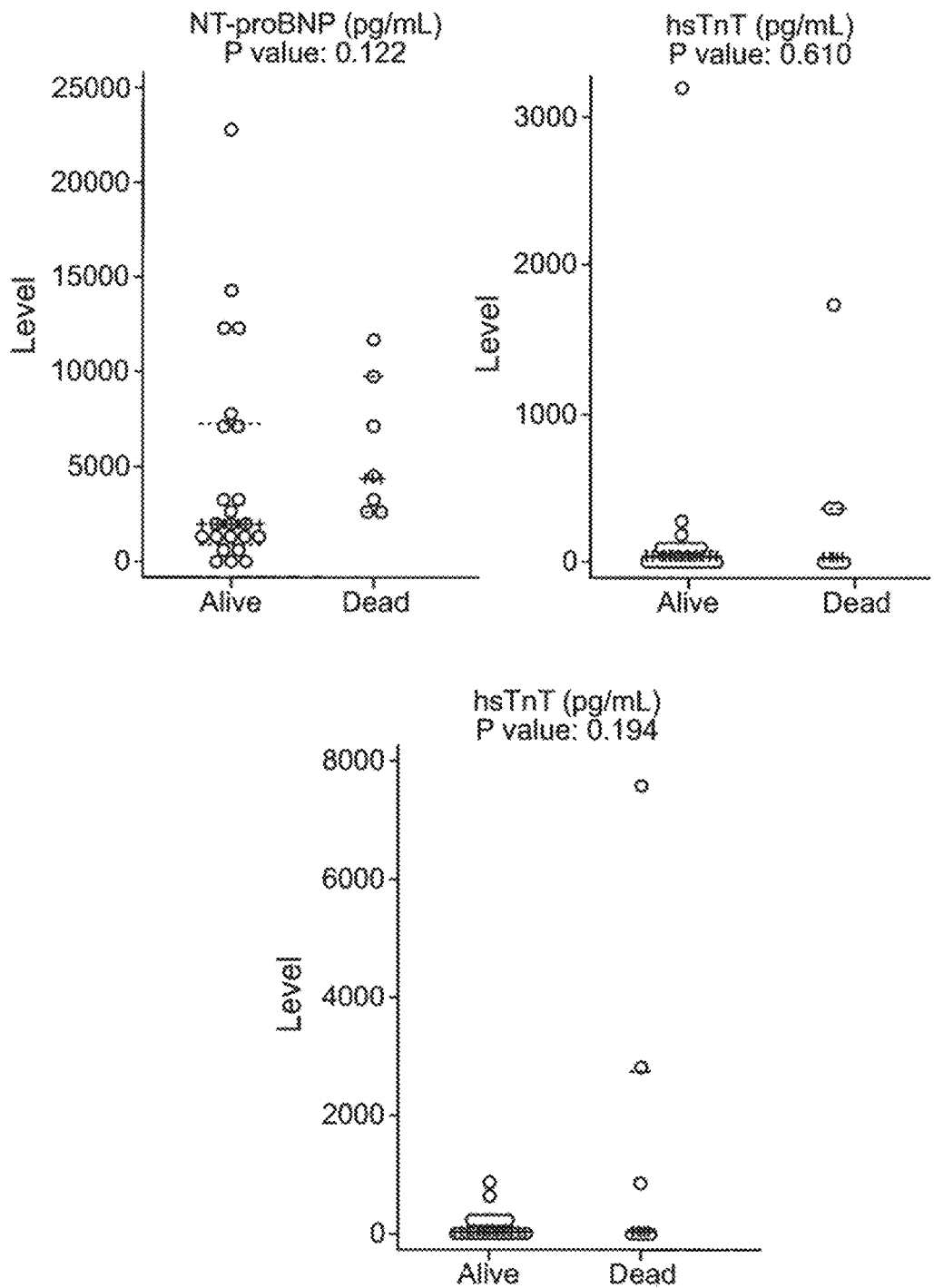
Figure 5:
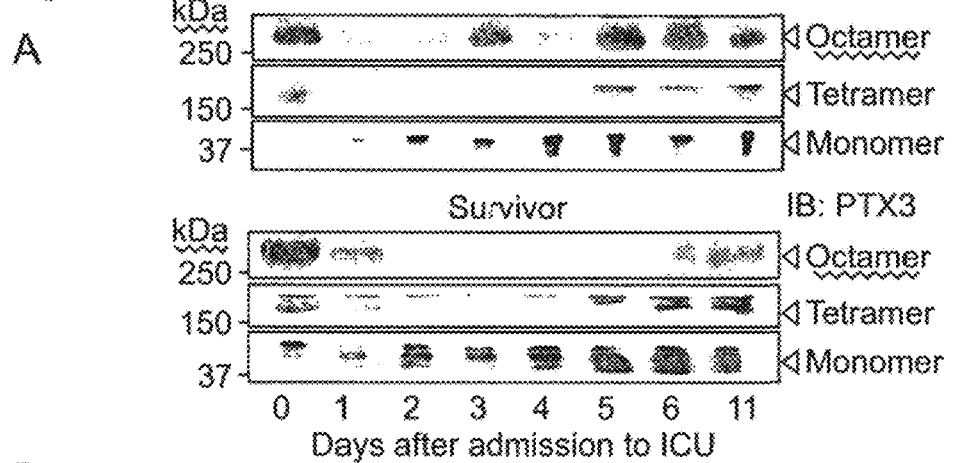
FIG. 5 shows association of pentraxin-3 (PTX3) oxidation with survival. A, Representative immunoblots of the development of the PTX3 oxidation state with time after admission in a non-surviving sepsis patient (upper panel) compared to a surviving sepsis patient (bottom panel). B, Monomeric, tetrameric and octameric PTX3 levels were quantified for each patient and time point using western immunoblot analysis performed under non-reducing conditions. * denotes statistical significant difference from baseline levels at day 0; $P<0.05$. C, Comparison of PTX3 oxidation levels between survivors and non-survivors on day 2 post admission to ICU.
Figure 5:
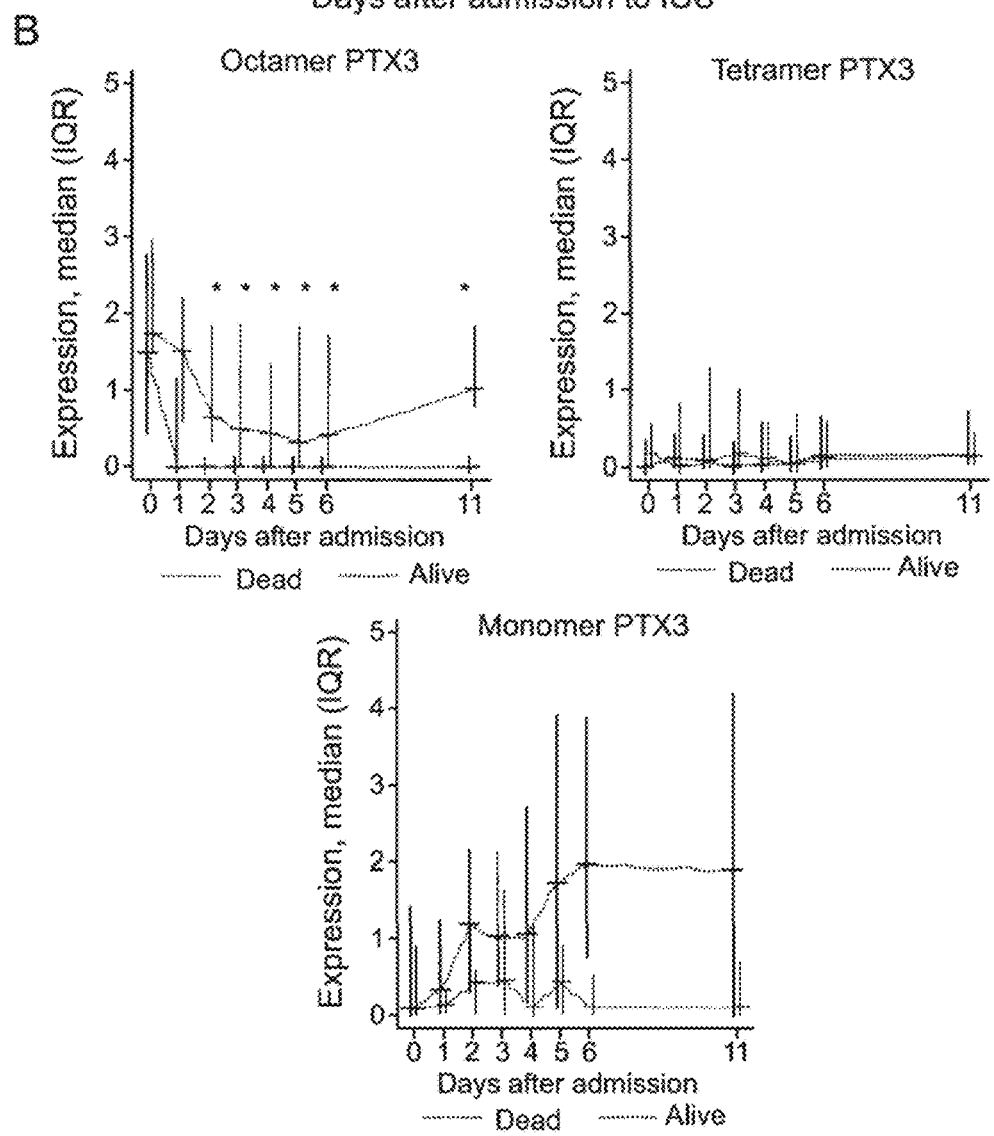
Figure 5:
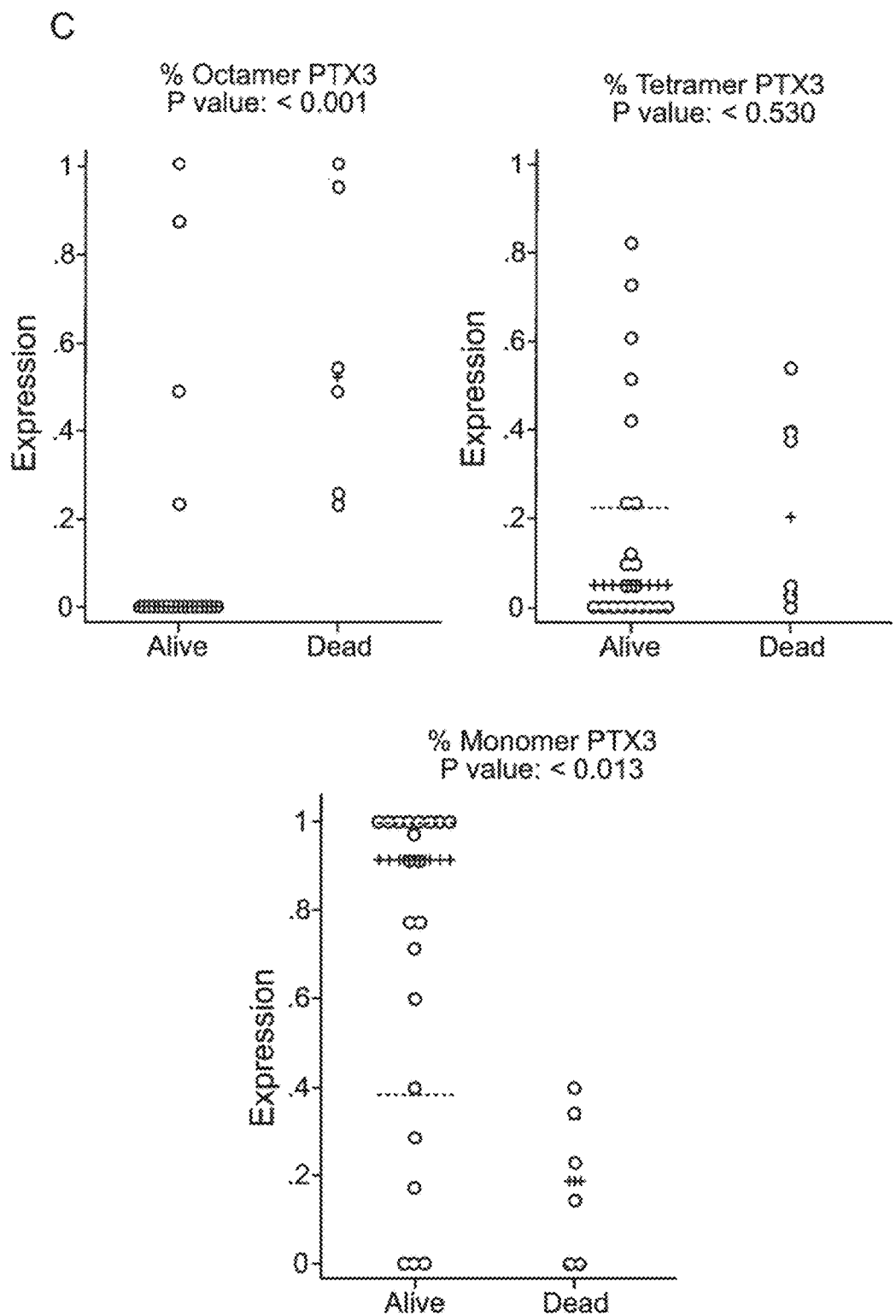
Figure 6:
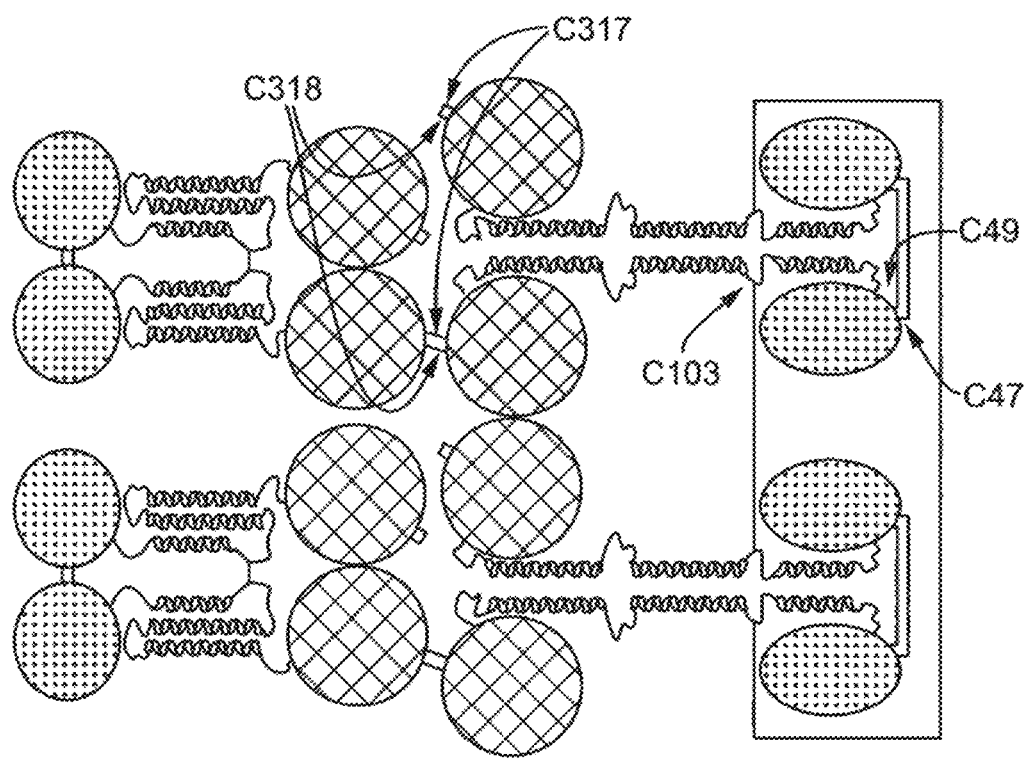
FIG. 6 shows antibodies that specifically recognize oxidized or reduced PTX3. The target sequence contains the two cysteines (Cys) that link the chains by a double disulfide: Cys 317 on one PTX3 monomer links with Cys 318 on another, and this occurs twice to form a double disulfide bond. The peptides have already been synthesised and a trial bridge has been successful. Once funding is in place, peptide synthesis will be scaled up for immunisation. We plan to generate first polyclonal, then monoclonal antibodies.
Figure 7:
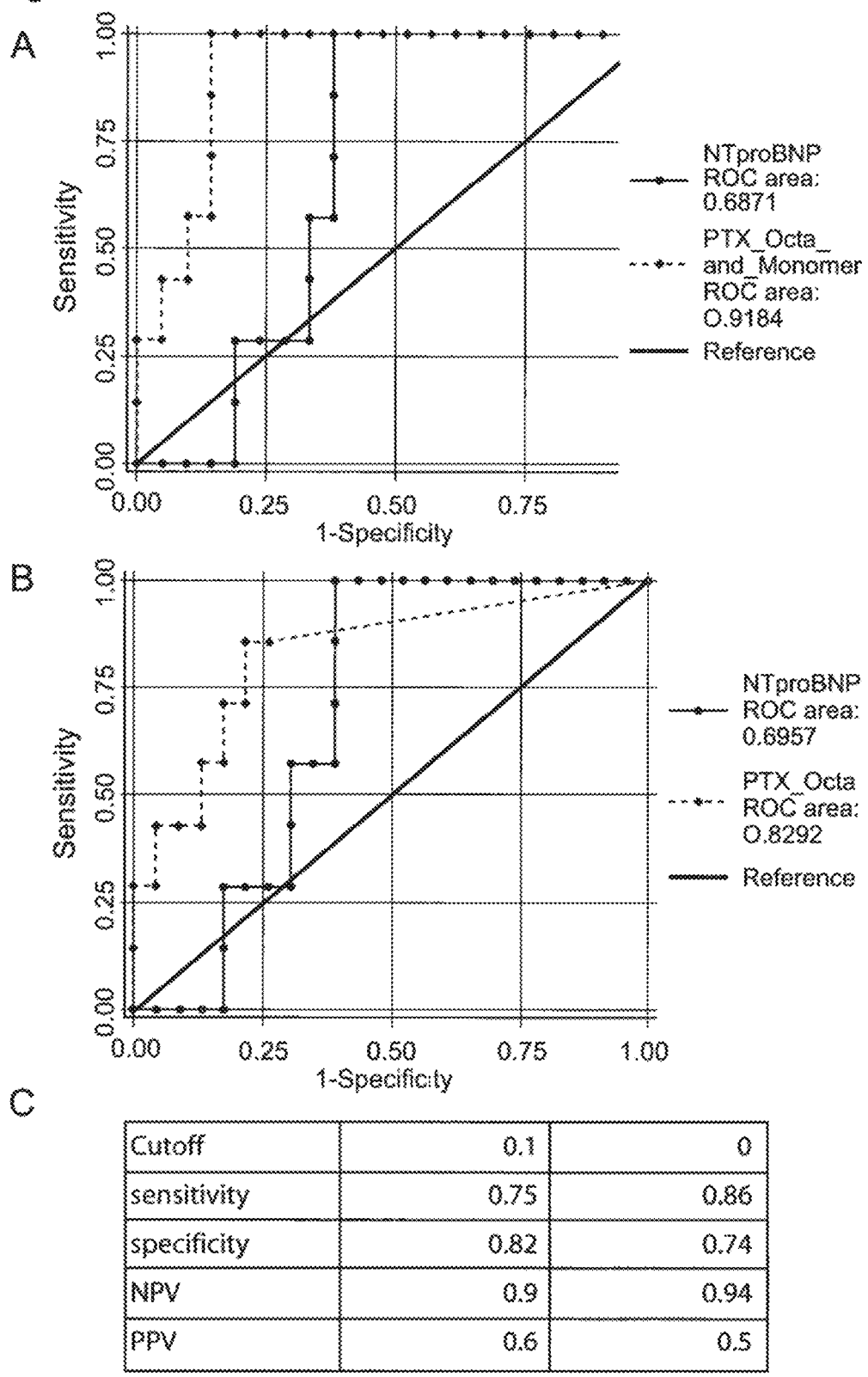
FIG. 7 shows ROC curves of PTX3 measurements compared to NT-proBNP. A) Discriminatory power of the oxidized to reduced PTX3 ratio. The area under the curve was 0.92 (95% CI, 0.82 to 1.00) for the combined measurement of PTX isoforms (octamer and monomer) and 0.69 (0.49 to 0.88) for N-terminal pro-B-type natriuretic peptide (NT-proBNP), a marker for left ventricular dysfunction that is frequently increased in SS. P-value for difference=0.02 B) Discriminatory power of octameric PTX3 only. C) Performance characteristics of octameric PTX3 as quantified by immunoblots under non-reducing conditions.

Monomer levels of PTX3 were inversely correlated to the cardiac damage markers high sensitivity troponin I (p=0.001), high sensitivity troponin T (p=0.067) and NT-proBNP (p=0.066) (FIG. 4A).

By comparison, unlike octameric and monomeric PTX3, the cardiac damage markers did not distinguish survivors and non-survivors (FIG. 4B).

Summary of Examples

AOF in sepsis is common, associated with high mortality, short-term morbidity, and significant chronic illness. Many biomarkers have been identified, but they lack specificity or sensitivity. Our tissue-based proteomics approach revealed PTX3 as the most differentially expressed protein. Importantly, we made the novel observation that circulating PTX3 was present in its oxidised octameric form and that its oxidation state could be a better prognostic biomarker in sepsis than total PTX3.

Oxidised PTX3 as Novel Biomarker.

Together with C-reactive protein (CRP) and serum amyloid protein (SAP), PTX3 belongs to the family of pentraxins. Although CRP is often used as a prognostic marker in inflammatory diseases, its prognostic value in sepsis is poor.[11] In contrast, high PTX3 plasma levels are correlated with severity of infection in patients with sepsis or septic shock.[12,13] PTX3 is barely detectable in plasma of healthy individuals (<2 ng/ml). Affected individuals show 2 ng/ml or more, with increases up to 200 ng/ml in sepsis depending on the severity of the disease[14]. For the first time, we quantified circulating levels of monomeric, tetrameric and octameric PTX3 in septic patients. On admission to ICU, there was no difference between survivors and non-survivors. By day 2, however, a reduction of octameric PTX3 to the monomeric form was associated with better chances of survival until 28 days of follow-up.

Function of Oxidised PTX3.

PTX3 plays an important role in regulating the innate immune response by contributing to opsonisation.[15] In mice, overexpression of PTX3 confers resistance to the lethal effects of LPS.[16] LPS injection elicits the secretion of several cytokines, including interleukin-1 and tumour necrosis factor alpha, two potent inducers of PTX3. Unlike the classical pentraxins CRP and SAP, PTX3 does not bind to phosphoethanolamine or phosphocholine but collagen-like Clq, the first component of the classical pathway of complement activation. Its capacity to bind Clq is mediated by the pentraxin domain and requires multimer formation.[10] As expected on the basis of Clq binding, high PTX3 may cause the consumption of $C_4$ and of the total complement haemolytic activity in serum.[10] Interestingly, there was a preponderance of the oxidised versus the reduced form of PTX3 with oxidised PTX3 accumulating in the heart, aorta, kidney and lung—organs that are known to be susceptible to septic complications. Less oxidized PTX3 was retained in the spleen and liver. This is consistent with previous reports that PTX3 is induced by LPS in vivo in heart and lung but not in liver.[17,18] Unlike the classical pentraxins CRP and SAP, PTX3 does not have the restricted liver inducibility but can be expressed by a variety of cells in response to lipopolysaccharide and inflammatory cytokines.[19,20]

Therapeutic Applications.

The causal mechanisms of AOF are not well understood and no effective mediator-targeted therapies of established AOF are available.[21] Numerous studies have tested novel therapeutics attempting to block key steps in the inflammatory processes associated with AOF. Unfortunately, all of these interventions have failed when tested in rigorous trials.[22] Consequently, except for antibiotics and source control of infection, the current management of AOF is supportive. No effective preventative therapies are currently available. Previous anti-inflammatory interventions mainly targeted circulating inflammatory cells or inflammatory mediators, i.e. by dialysis. This may be insufficient if the inflammation resides within the tissue. The observed retention of oxidized PTX3 in the Triton-insoluble fraction and the inverse correlation of monomeric plasma PTX3 with cardiac damage markers support the concept that inflammation and tissue damage may be perpetuated locally. Thus, in addition to targeting circulating mediators of inflammation, resolving the inflammation within the tissues may be an alternative strategy in the prevention of AOF.

Thus, prior art tests measure total PTX3 whereas we show that the oxidation state of PTX3 is more important.

We successfully translated proteomic findings in a mouse model of sepsis to biomarker studies in human patients admitted to ICU. We provide proof-of-principle that changes in the oxidation state of PTX3 allow the identification of at-risk patients and/or aids prognosis/prediction of clinical outcome, particularly adverse clinical outcome. Another benefit of the invention is that sepsis patients at risk of developing AOF can be identified early, which can help to 'personalise' critical care medicine.

REFERENCES

1. Rittirsch D, Flierl M A, Ward P A. Harmful molecular mechanisms in sepsis. Nature reviews. *Immunology.* 2008; 8:776-787
2. Anderson N L, Anderson N G. The human plasma proteome: History, character, and diagnostic prospects. *Mol Cell Proteomics.* 2002; 1:845-867
3. Anderson L, Hunter C L. Quantitative mass spectrometric multiple reaction monitoring assays for major plasma proteins. *Mol Cell Proteomics.* 2006; 5:573-588
4. Jacquet S, Yin X, Sicard P, Clark J, Kanaganayagam G S, Mayr M, Marber M S.
   Identification of cardiac myosin-binding protein c as a candidate biomarker of myocardial infarction by proteomics analysis. *Mol Cell Proteomics.* 2009; 8:2687-2699
5. Mayr M, Zhang J, Greene A S, Gutterman D, Perloff J, Ping P. Proteomics-based development of biomarkers in cardiovascular disease: Mechanistic, clinical, and therapeutic insights. *Mol Cell Proteomics.* 2006; 5:1853-1864
6. Mayr M, Zampetaki A, Willeit P, Willeit J, Kiechl S. Micrornas within the continuum of postgenomics biomarker discovery. *Arterioscler Thromb Vasc Biol.* 2013; 33:206-214
7. Didangelos A, Stegemann C, Mayr M. The-omics era: Proteomics and lipidomics in vascular research. *Atherosclerosis.* 2012; 221:12-17
8. Bottazzi B, Doni A, Garlanda C, Mantovani A. An integrated view of humoral innate immunity: Pentraxins as a paradigm. *Annual review of immunology.* 2010; 28:157-183
9. Inforzato A, Rivieccio V, Morreale A P, Bastone A, Salustri A, Scarchilli L, Verdoliva A, Vincenti S, Gallo G, Chiapparino C, Pacello L, Nucera E, Serlupi-Crescenzi O, Day A J, Bottazzi B, Mantovani A, De Santis R, Salvatori G. Structural characterization of ptx3 disulfide bond network and its multimeric status in cumulus matrix organization. *The Journal of biological chemistry.* 2008; 283: 10147-10161
10. Bottazzi B, Vouret-Craviari V, Bastone A, De Gioia L, Matteucci C, Peri G, Spreafico F, Pausa M, D'Ettorre C, Gianazza E, Tagliabue A, Salmona M, Tedesco F, Introna M, Mantovani A. Multimer formation and ligand recognition by the long pentraxin ptx3. Similarities and differences with the short pentraxins c-reactive protein and serum amyloid p component. *J Biol Chem.* 1997; 272: 32817-32823

11. Silvestre J, Povoa P, Coelho L, Almeida E, Moreira P, Fernandes A, Mealha R, Sabino H. Is c-reactive protein a good prognostic marker in septic patients? *Intensive care medicine.* 2009; 35:909-913
12. Huttunen R, Aittoniemi J. New concepts in the pathogenesis, diagnosis and treatment of bacteremia and sepsis. *The Journal of infection.* 2011; 63:407-419
13. Mauri T, Bellani G, Patroniti N, Coppadoro A, Peri G, Cuccovillo I, Cugno M, Iapichino G, Gattinoni L, Pesenti A, Mantovani A. Persisting high levels of plasma pentraxin 3 over the first days after severe sepsis and septic shock onset are associated with mortality. *Intensive care medicine.* 2010; 36:621-629
14. Daigo K, Yamaguchi N, Kawamura T, Matsubara K, Jiang S, Ohashi R, Sudou Y, Kodama T, Naito M, Inoue K, Hamakubo T. The proteomic profile of circulating pentraxin 3 (ptx3) complex in sepsis demonstrates the interaction with azurocidin 1 and other components of neutrophil extracellular traps. *Mol Cell Proteomics.* 2012; 11:M111 015073
15. Bottazzi B, Garlanda C, Cotena A, Moalli F, Jaillon S, Deban L, Mantovani A. The long pentraxin ptx3 as a prototypic humoral pattern recognition receptor: Interplay with cellular innate immunity. *Immunological reviews.* 2009; 227:9-18
16. Dias A A, Goodman A R, Dos Santos J L, Gomes R N, Altmeyer A, Bozza P T, Horta M F, Vilcek J, Reis L F. Tsg-14 transgenic mice have improved survival to endotoxemia and to clp-induced sepsis. Journal of leukocyte biology. 2001; 69:928-936
17. Lee G W, Goodman A R, Lee T H, Vilcek J. Relationship of tsg-14 protein to the pentraxin family of major acute phase proteins. *J Immunol.* 1994; 153:3700-3707
18. Introna M, Alles V V, Castellano M, Picardi G, De Gioia L, Bottazzai B, Peri G, Breviario F, Salmona M, De Gregorio L, Dragani T A, Srinivasan N, Blundell T L, Hamilton T A, Mantovani A. Cloning of mouse ptx3, a new member of the pentraxin gene family expressed at extrahepatic sites. *Blood.* 1996; 87:1862-1872
19. Breviario F, d'Aniello E M, Golay J, Peri G, Bottazzi B, Bairoch A, Saccone S, Marzella R, Predazzi V, Rocchi M, et al. Interleukin-1-inducible genes in endothelial cells. Cloning of a new gene related to c-reactive protein and serum amyloid p component. *The Journal of biological chemistry.* 1992; 267:22190-22197
20. Alles V V, Bottazzi B, Peri G, Golay J, Introna M, Mantovani A. Inducible expression of ptx3, a new member of the pentraxin family, in human mononuclear phagocytes. *Blood.* 1994; 84:3483-3493
21. Marshall J C. Such stuff as dreams are made on: Mediator-directed therapy in sepsis. Nature reviews. *Drug discovery.* 2003; 2:391-405
22. Sweeney D A, Danner R L, Eichacker P Q, Natanson C. Once is not enough: Clinical trials in sepsis. *Intensive care medicine.* 2008; 34:1955-1960

---

The invention claimed is:

1. A method of collecting information useful in predicting survival or non-survival of a subject who is suspected of having an inflammatory disease, the method comprising:
    providing a sample from the subject, the sample including blood, serum, or plasma;
    determining the level of octameric PTX3 in the sample, the determining the level of octameric PTX3 including measuring the total amount of PTX3 present, and measuring the amount of octameric PTX3 and monomeric PTX3 present, wherein the amounts of monomeric PTX3 and octameric PTX3 are determined by:
    (a) separating the proteins in the sample at least under non-reducing conditions; and
    (b) measuring the amounts of monomeric PTX3 and octameric PTX3 by quantifying the amounts of those forms of PTX3 as separated in step (a); and
    calculating a ratio of octameric PTX3 to monomeric PTX3, wherein the ratio of the octameric PTX3 to the monomeric PTX3 is determined to provide greater discriminatory power compared to NT-proBNP as indicated by ROC curves, and if the ratio of the octameric PTX3 to monomeric PTX3 is greater than 50%, then the subject is identified as a likely non-survivor from the inflammatory disease.

2. A method of collecting information useful in predicting survival or non-survival of a subject who is suspected of having an inflammatory disease, the method comprising:
    providing a sample from the subject, the sample including one of blood, serum, and plasma; and
    determining the level of octameric PTX3 in the sample, wherein if the proportion of octameric PTX3 as compared to a reference standard is greater than 50%, a reduced likelihood of survival from the inflammatory disease is indicated,
    wherein the reference standard is a numerical value with a proportion of octameric PTX3 based on an actual sample analyzed and derived from a healthy person absent the inflammatory disease, and
    wherein tissue-based proteomics indicates that the octameric PTX3 is oxidized octameric PTX3, which is an oxidized form.

3. The method according to claim 2, wherein the inflammatory disease is one of sepsis, cardiovascular disease and a rheumatoid disease.

4. The method according to claim 1,
    wherein tissue-based proteomics indicates that the octameric PTX3 is oxidized octameric PTX3, which is an oxidized form.

5. The method according to claim 1, wherein the step (b) comprises blotting the separated proteins on to a membrane and quantifying the amounts of those forms of PTX3 on the membrane.

6. The method according to claim 1, wherein the amounts of monomeric PTX3 and octameric PTX3 are determined by mass spectrometry.

7. The method according to claim 1, wherein the inflammatory disease is one of sepsis, cardiovascular disease and a rheumatoid disease.

8. The method according to claim 7, wherein the inflammatory disease is sepsis.

9. The method according to claim 1, wherein the subject is experiencing oxidative stress in the inflammatory disease.

10. The method according to claim 1, wherein the sample includes plasma.

11. The method according to claim 1, wherein the measurement at step (b) is repeated at a predetermined time interval.

12. The method according to claim 11, wherein the time interval is daily.

13. A method of collecting information useful in aiding the prognosis of a subject suffering from oxidative stress, comprising:
   performing the method according to claim 1, wherein the proportion of octameric PTX3 being greater than 50% indicates a probable non-survivor due to an inflammatory disease,
   wherein the inflammatory disease is one of sepsis, cardiovascular disease and a rheumatoid disease.

* * * * *

UNITED STATES PATENT AND TRADEMARK OFFICE
CERTIFICATE OF CORRECTION

PATENT NO.        : 10,234,463 B2
APPLICATION NO.   : 14/893341
DATED             : March 19, 2019
INVENTOR(S)       : Manuel Mayr et al.

It is certified that error appears in the above-identified patent and that said Letters Patent is hereby corrected as shown below:

On the Title Page

Item (22) should be corrected as follows:
May 22, 2014

Signed and Sealed this
Twenty-sixth Day of November, 2019

Andrei Iancu
*Director of the United States Patent and Trademark Office*